United States Patent
Simon et al.

(10) Patent No.: US 10,232,178 B2
(45) Date of Patent: Mar. 19, 2019

(54) NON-INVASIVE MAGNETIC OR ELECTRICAL NERVE STIMULATION TO TREAT OR PREVENT DEMENTIA

(71) Applicant: Electrocore, LLC, Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: Electrocore, Inc., Basking Ridge, NJ (US)

( * ) Notice: Subject to any disclaimer, the term of this patent is extended or adjusted under 35 U.S.C. 154(b) by 0 days.

(21) Appl. No.: 13/671,859

(22) Filed: Nov. 8, 2012

(65) Prior Publication Data

US 2013/0066392 A1    Mar. 14, 2013

Related U.S. Application Data

(63) Continuation-in-part of application No. 13/183,765, filed on Jul. 15, 2011, now Pat. No. 8,874,227, which
(Continued)

(51) Int. Cl.
*A61N 1/18* (2006.01)
*A61N 1/36* (2006.01)
(Continued)

(52) U.S. Cl.
CPC ..... *A61N 1/36053* (2013.01); *A61N 1/36014* (2013.01); *A61N 1/36025* (2013.01);
(Continued)

(58) Field of Classification Search
CPC .............. A61N 1/36053; A61N 1/3787; A61N 1/3601; A61N 1/36082; A61N 1/0456; A61N 1/36025
(Continued)

(56) References Cited

U.S. PATENT DOCUMENTS

| | | |
|---|---|---|
| 4,196,737 A | 4/1980 | Bevilacqua |
| 4,989,605 A | 2/1991 | Rossen |

(Continued)

FOREIGN PATENT DOCUMENTS

| | | |
|---|---|---|
| EP | 2777764 | 8/2015 |
| KR | 101242190 | 3/2013 |

(Continued)

OTHER PUBLICATIONS

International Search Report and Written Opinion dated Mar. 26, 2008 in related PCT Application No. PCT/US2006/042752 filed Nov. 1, 2006 (7 pages).

(Continued)

*Primary Examiner* — Niketa I Patel
*Assistant Examiner* — Minh Duc Pham
(74) *Attorney, Agent, or Firm* — Dentons US LLP

(57) ABSTRACT

Devices, systems and methods are disclosed for treating or preventing dementia, such as Alzheimer's disease. The methods comprise transmitting impulses of energy non-invasively to selected nerve fibers, particularly those in a vagus nerve, that modulate the activity of a patient's locus ceruleus. The transmitted energy impulses, comprising magnetic and/or electrical energy, stimulate the selected nerve fibers to cause the locus ceruleus to release norepinephrine into regions of the brain that contain beta-amyloids. The norepinephrine counteracts neuroinflammation that would damage neurons in those regions and the locus ceruleus, thereby arresting or slowing the progression of the disease in the patient.

16 Claims, 11 Drawing Sheets

Related U.S. Application Data is a continuation-in-part of application No. 13/183,721, filed on Jul. 15, 2011, now Pat. No. 8,676,324, which is a continuation-in-part of application No. 13/109,250, filed on May 17, 2011, now Pat. No. 8,676,330, which is a continuation-in-part of application No. 13/075,746, filed on Mar. 30, 2011, now Pat. No. 8,874,205, which is a continuation-in-part of application No. 13/024,727, filed on Feb. 10, 2011, now Pat. No. 9,089,719, which is a continuation-in-part of application No. 13/005,005, filed on Jan. 12, 2011, now Pat. No. 8,868,177, which is a continuation-in-part of application No. 12/964,050, filed on Dec. 9, 2010, now abandoned, which is a continuation-in-part of application No. 12/859,568, filed on Aug. 19, 2010, now Pat. No. 9,037,247, which is a continuation-in-part of application No. 12/408,131, filed on Mar. 20, 2009, now Pat. No. 8,812,112, and a continuation-in-part of application No. 12/612,177, filed on Nov. 4, 2009, now Pat. No. 8,041,428.

(60) Provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(51) Int. Cl.
*A61N 1/40* (2006.01)
*A61N 2/00* (2006.01)
*A61N 2/02* (2006.01)
*A61B 5/0476* (2006.01)
*A61B 5/00* (2006.01)

(52) U.S. Cl.
CPC .............. *A61N 1/40* (2013.01); *A61N 2/006* (2013.01); *A61N 2/02* (2013.01); *A61B 5/0476* (2013.01); *A61B 5/4082* (2013.01); *A61B 5/4088* (2013.01); *A61B 5/4094* (2013.01); *A61B 5/4833* (2013.01); *A61B 5/4836* (2013.01)

(58) Field of Classification Search
USPC .......................................................... 607/61
See application file for complete search history.

(56) References Cited

U.S. PATENT DOCUMENTS

| | | | |
|---|---|---|---|
| 5,458,141 A | 10/1995 | Neil | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 7,734,340 B2 | 6/2010 | De Ridder | |
| 7,797,041 B2 | 9/2010 | Libbus et al. | |
| 2002/0099417 A1 | 7/2002 | Naritoku et al. | |
| 2002/0099426 A1* | 7/2002 | Silverstone | A61N 1/326 607/72 |
| 2002/0183237 A1 | 12/2002 | Puskas | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0027284 A1* | 2/2005 | Lozano | A61M 5/14276 604/890.1 |
| 2005/0065574 A1 | 3/2005 | Rezai | |
| 2005/0113630 A1 | 5/2005 | Fox et al. | |
| 2005/0137644 A1 | 6/2005 | Bojeva et al. | |
| 2005/0154426 A1* | 7/2005 | Boveja | A61N 1/36007 607/45 |
| 2005/0216062 A1 | 9/2005 | Herbst | |
| 2005/0267544 A1 | 12/2005 | Lee et al. | |
| 2006/0074284 A1 | 4/2006 | Juola et al. | |
| 2006/0074450 A1 | 4/2006 | Boveja | |
| 2006/0100668 A1* | 5/2006 | Ben-David | A61N 1/36071 607/2 |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0179557 A1* | 8/2007 | Maschino | A61N 1/36071 607/45 |
| 2007/0276449 A1 | 11/2007 | Gunter et al. | |
| 2007/0293917 A1* | 12/2007 | Thompson | A61N 1/0456 607/72 |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0051852 A1* | 2/2008 | Dietrich | A61H 39/002 607/45 |
| 2008/0077192 A1 | 3/2008 | Harry et al. | |
| 2008/0114199 A1 | 5/2008 | Riehl et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0112283 A1 | 4/2009 | Kriksunov et al. | |
| 2009/0132018 A1 | 5/2009 | Diubaldi et al. | |
| 2009/0143831 A1* | 6/2009 | Huston | A61N 1/36053 607/2 |
| 2009/0157149 A1 | 6/2009 | Wahlgren et al. | |
| 2009/0234417 A1 | 9/2009 | Pastena et al. | |
| 2009/0234419 A1* | 9/2009 | Maschino | A61M 5/14276 607/45 |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0137381 A1* | 6/2011 | Lee | A61N 1/0529 607/62 |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0245486 A1 | 9/2013 | Simon et al. | |
| 2014/0005743 A1 | 1/2014 | Giuffrida et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| WO | WO 1993/01862 | 2/1993 |
| WO | WO2005/007120 | 1/2005 |
| WO | WO2007/058780 | 5/2007 |
| WO | WO2007/092062 | 8/2007 |
| WO | WO2008/042902 | 4/2008 |
| WO | WO 2009/021080 | 2/2009 |

(56) References Cited

FOREIGN PATENT DOCUMENTS

| WO | WO 2009/135693 | 11/2009 |
|---|---|---|
| WO | WO2013066135 | 5/2013 |

OTHER PUBLICATIONS

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 9, 2013 (10 pages).

Greicius, Funtional Connectivity in the resting brain: A network analysis of the default mode hypothesis, PNAS, Jan. 2003, vol. 100, No. 1, pp. 253-258.

Heneka et al., Locus ceruleus controls Alzheimer's disease pathology by modulating microglial functions through norepinephrine, Proc Natl Acad Sci USA, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Aug. 25, 2015 in related Application No. PCT/US15/31847 filed May 20, 2015 (10 pages).

Europe Office Action dated Apr. 24, 2018 in related Application No. 15796247.3 filed May 20, 2015 (6 pages).

KR101242190 dated Mar. 25, 2013, Espacenet computer generated English translation (11 pages).

Europe Office Action dated Jul. 26, 2018 in related Application No. 11818591.7 filed Aug. 12, 2011 (8 pages).

\* cited by examiner

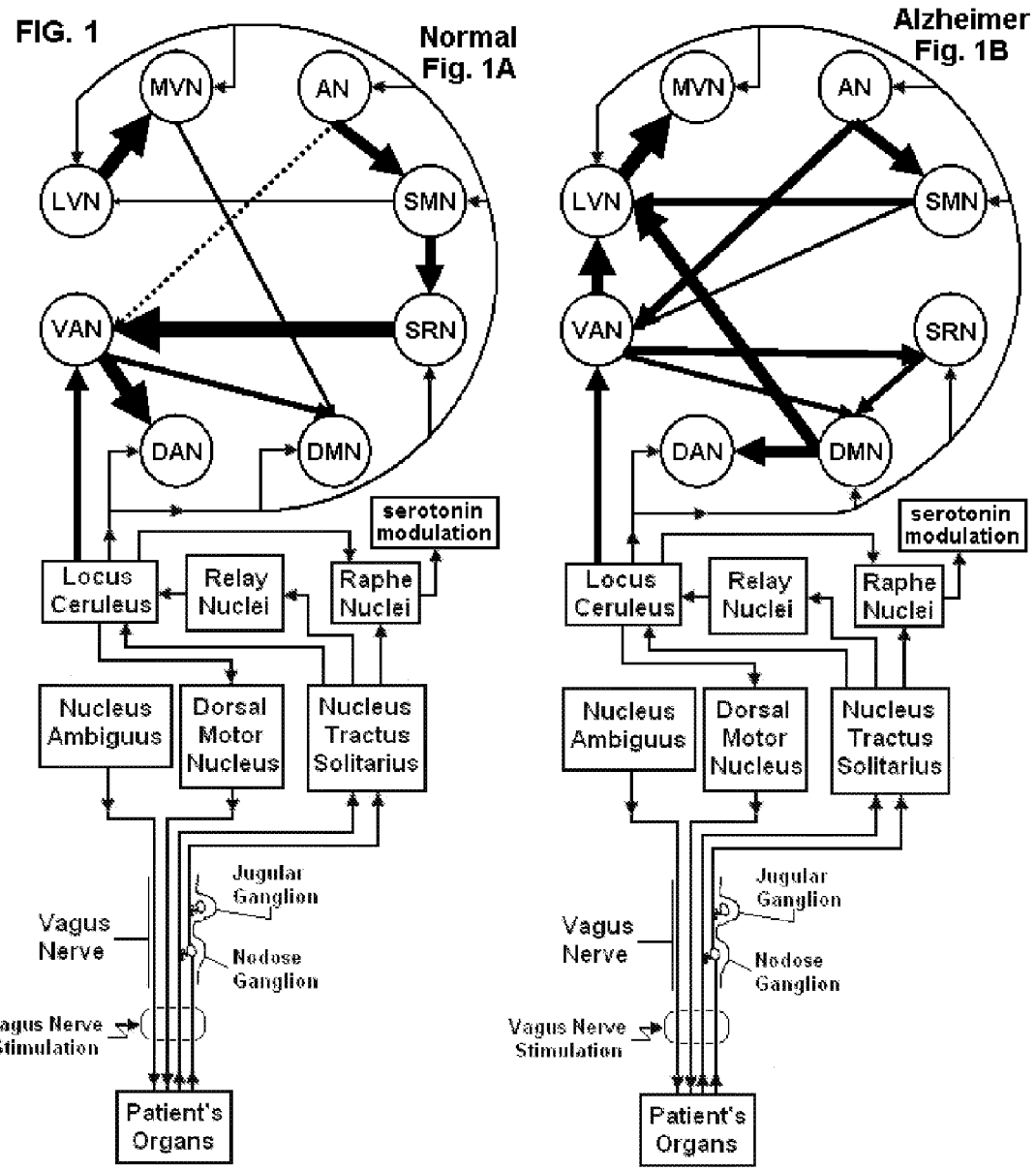

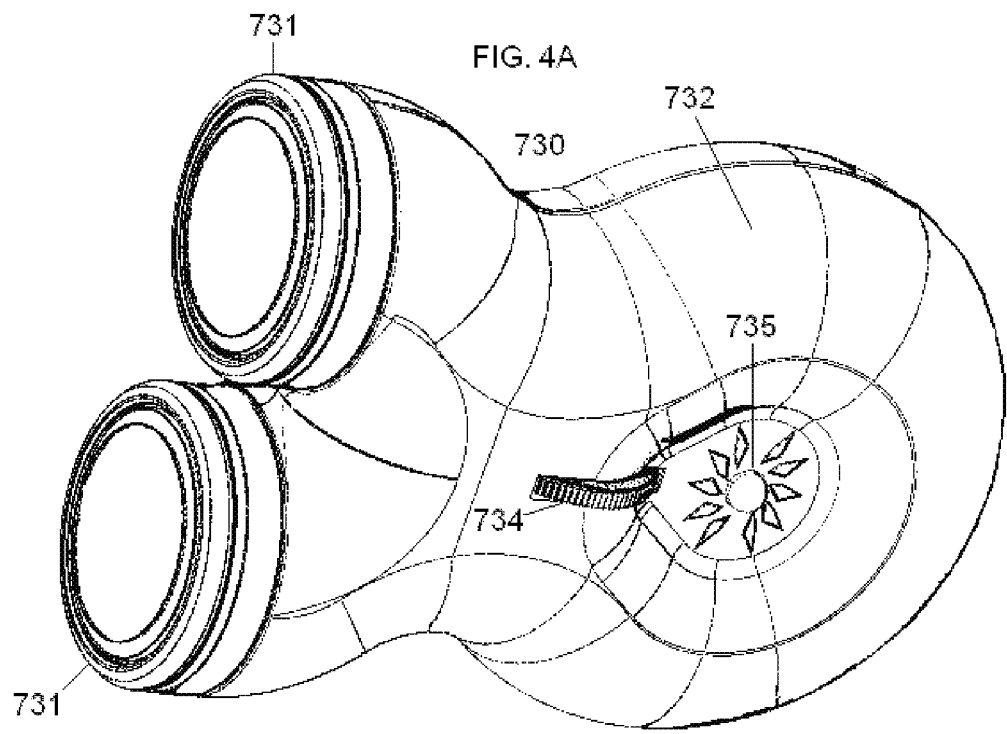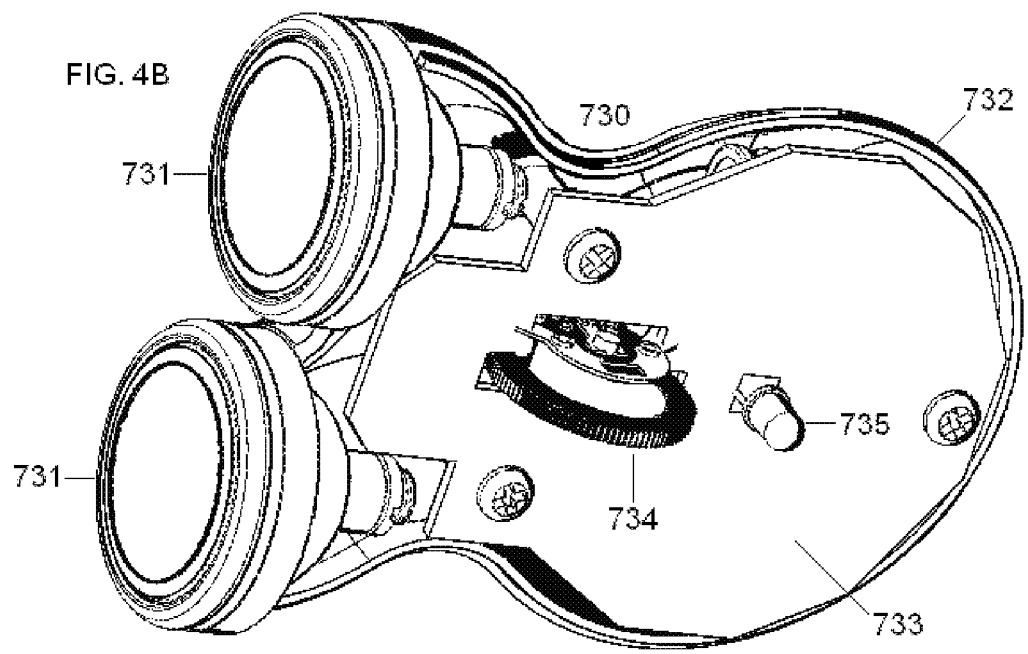

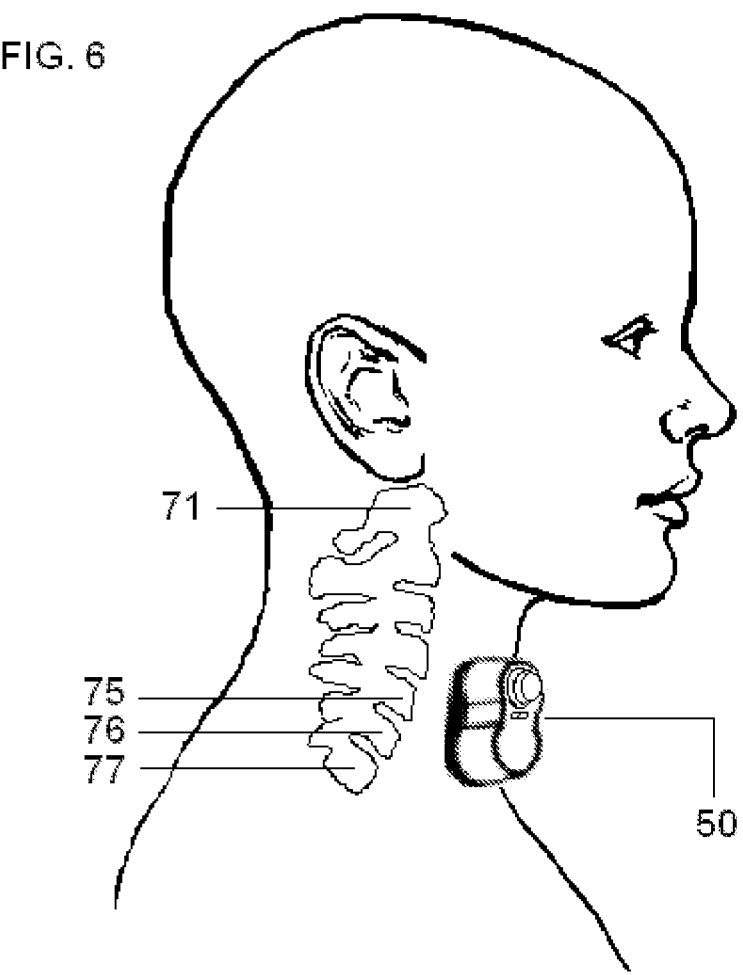

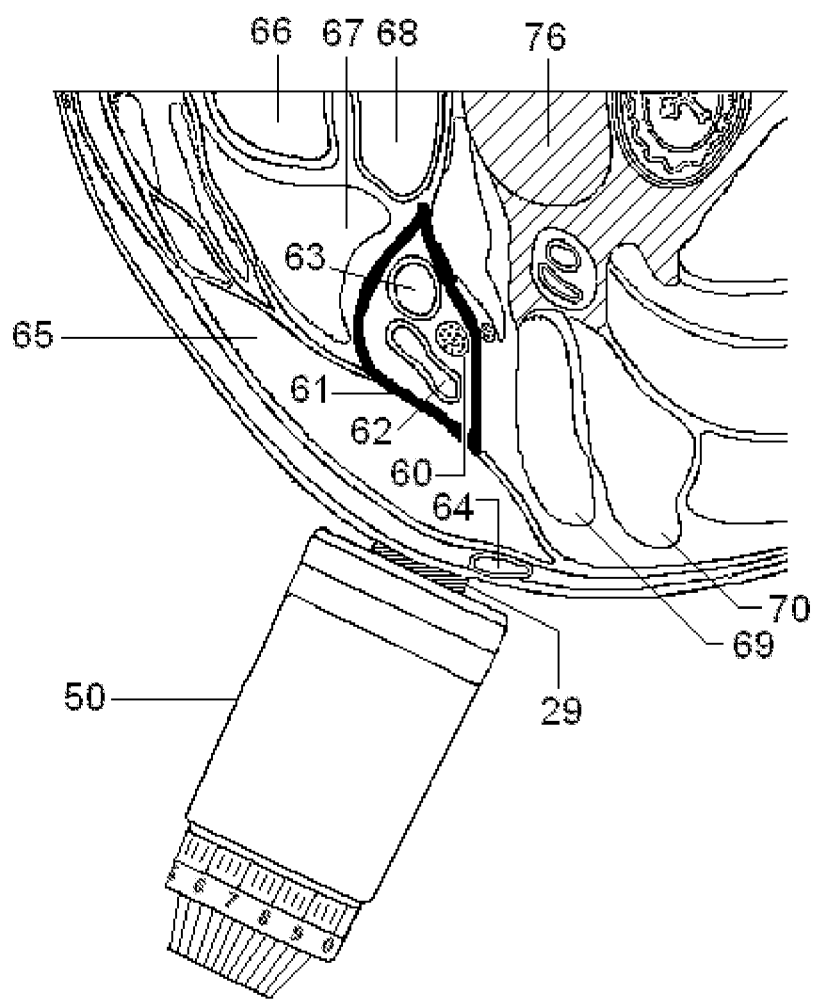

NON-INVASIVE MAGNETIC OR ELECTRICAL NERVE STIMULATION TO TREAT OR PREVENT DEMENTIA

CROSS REFERENCE TO RELATED APPLICATIONS

This application is a continuation-in-part of U.S. patent application Ser. No. 13/183,765 filed Jul. 15, 2011, Pub. No. 2011-0276112, which claims the benefit of priority of U.S. Provisional Patent Application No. 61/488,208 filed May 20, 2011 and is a continuation-in-part to U.S. patent application Ser. No. 13/183,721 filed Jul. 15, 2011, Pub. No. 2011-0276107, which claims the benefit of priority of U.S. Provisional Patent Application No. 61/487,439 filed May 18, 2011 and is a continuation-in-part of U.S. patent application Ser. No. 13/109,250 filed May 17, 2011, Pub. No. 2011-0230701, which claims the benefit of priority of U.S. Provisional Patent Application No. 61/471,405 filed Apr. 4, 2011 and is a continuation-in-part of U.S. patent application Ser. No. 13/075,746 filed Mar. 30, 2011, Pub. No. 2011-0230938 which claims the benefit of priority of U.S. provisional patent application 61/451,259 filed Mar. 10, 2011 and is a continuation-in-part of U.S. patent application Ser. No. 13/024,727 filed Feb. 10, 2011, Pub No. 2011-0190569, which is a continuation-in-part of U.S. patent application Ser. No. 13/005,005 filed Jan. 12, 2011, Pub. No. 2011-0152967 which is a continuation-in-part of U.S. patent application Ser. No. 12/964,050 filed Dec. 9, 2010, Pub No. 2011-0125203, which claims the benefit of priority of U.S. Provisional Patent Application No. 61/415,469 filed Nov. 19, 2010 and is a continuation-in-part of U.S. patent application Ser. No. 12/859,568 filed Aug. 9, 2010, Pub. No. 2011-0046432, which is a continuation-in-part of U.S. patent application Ser. No. 12/408,131 filed Mar. 20, 2009, Pub. No. 2009-0187231 and a continuation-in-part application of U.S. patent application Ser. No. 12/612,177 filed Nov. 9, 2009 now U.S. Pat. No. 8,041,428 issued Oct. 18, 2011 the entire disclosures of which are hereby incorporated by reference.

BACKGROUND OF THE INVENTION

The field of the present invention relates to the delivery of energy impulses (and/or fields) to bodily tissues for therapeutic purposes. The invention relates more specifically to devices and methods for treating conditions associated with dementia, particularly Alzheimer's disease. The energy impulses (and/or fields) that are used to treat those conditions comprise electrical and/or electromagnetic energy, delivered non-invasively to the patient.

The use of electrical stimulation for treatment of medical conditions is well known. For example, electrical stimulation of the brain with implanted electrodes has been approved for use in the treatment of various conditions, including pain and movement disorders such as essential tremor and Parkinson's disease.

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92 (2001):505-513; U.S. Pat. No. 6,871,099 entitled Fully implantable microstimulator for spinal cord stimulation as a therapy for chronic pain, to Whitehurst, et al].

The form of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES D A, Brown V. J. Vagal nerve stimulation: a review of its applications and potential mechanisms that mediate its clinical effects. Neurosci Biobehav Rev 29 (2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4; ANDREWS, R. J. Neuromodulation. I. Techniques-deep brain stimulation, vagus nerve stimulation, and transcranial magnetic stimulation. Ann. N.Y. Acad. Sci. 993 (2003): 1-13; LABINER, D. M., Ahern, G. L. Vagus nerve stimulation therapy in depression and epilepsy: therapeutic parameter settings. Acta. Neurol. Scand. 115 (2007): 23-33].

Many such therapeutic applications of electrical stimulation involve the surgical implantation of electrodes within a patient. In contrast, devices used for the medical procedures that are disclosed herein do not involve surgery. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g, beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2, 2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, An electric field is induced at a distance causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. In contrast, the magnetic stimulators that are disclosed herein are relatively simpler devices that use considerably smaller currents within the stimulator coils. Accordingly, they are intended to satisfy the need for simple-to-use and less expensive non-invasive magnetic stimulation devices, for use in treating dementia, as well as use in treating other conditions.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In the present invention, noninvasive vagus nerve electrical stimulation and/or magnetic stimulation are used to treat neurodegenerative diseases. Neurodegenerative diseases result from the deterioration of neurons, causing brain dysfunction. The diseases are loosely divided into two groups—conditions affecting memory that are ordinarily related to dementia and conditions causing problems with movements. The most widely known neurodegenerative diseases include Alzheimer (or Alzheimer's) disease and its precursor mild cognitive impairment (MCI), Parkinson's disease (including Parkinson's disease dementia), and multiple sclerosis.

Less well-known neurodegenerative diseases include adrenoleukodystrophy, AIDS dementia complex, Alexander disease, Alper's disease, amyotrophic lateral sclerosis (ALS), ataxia telangiectasia, Batten disease, bovine spongiform encephalopathy, Canavan disease, cerebral amyloid angiopathy, cerebellar ataxia, Cockayne syndrome, corticobasal degeneration, Creutzfeldt-Jakob disease, diffuse myelinoclastic sclerosis, fatal familial insomnia, Fazio-Londe disease, Friedreich's ataxia, frontotemporal dementia or lobar degeneration, hereditary spastic paraplegia, Huntington disease, Kennedy's disease, Krabbe disease, Lewy body dementia, Lyme disease, Machado-Joseph disease, motor neuron disease, Multiple systems atrophy, neuroacanthocytosis, Niemann-Pick disease, Pelizaeus-Merzbacher Disease, Pick's disease, primary lateral sclerosis including its juvenile form, progressive bulbar palsy, progressive supranuclear palsy, Refsum's disease including its infantile form, Sandhoff disease, Schilder's disease, spinal muscular atrophy, spinocerebellar ataxia, Steele-Richardson-Olszewski disease, subacute combined degeneration of the spinal cord, survival motor neuron spinal muscular atrophy, Tabes dorsalis, Tay-Sachs disease, toxic encephalopathy, transmissible spongiform encephalopathy, Vascular dementia, and X-linked spinal muscular atrophy, as well as idiopathic or cryptogenic diseases as follows: synucleinopathy, progranulinopathy, tauopathy, amyloid disease, prion disease, protein aggregation disease, and movement disorder. A more comprehensive listing may be found at the web site (www) of the National Institute of Neurological Disorders and Stroke (ninds) of the National Institutes of Health (nih) of the United States government (gov). It is understood that such diseases often go by more than one name and that a disease classification may oversimplify pathologies that occur in combination or that are not archetypical.

Despite the fact that at least some aspect of the pathology of each of the neurodegenerative diseases mentioned above is different from the other diseases, their pathologies ordinarily share other features, so that they may be considered as a group. Furthermore, aspects of their pathologies that they have in common often make it possible to treat them with similar therapeutic methods. Thus, many publications describe features that neurodegenerative diseases have in common [Dale E. BREDESEN, Rammohan V. Rao and Patrick Mehlen. Cell death in the nervous system. Nature 443 (2006): 796-802; Christian HAASS. Initiation and propagation of neurodegeneration. Nature Medicine 16(11, 2010): 1201-1204; Eng H LO. Degeneration and repair in central nervous system disease. Nature Medicine 16(11, 2010):1205-1209; Daniel M. SKOVRONSKY, Virginia M.-Y. Lee, and John Q. TROJANOWSKI. Neurodegenerative Diseases New Concepts of Pathogenesis and Their Therapeutic Implications. Annu. Rev. Pathol. Mech. Dis. 1 (2006): 151-70; Michael T. LIN and M. Flint Beal. Mitochondrial dysfunction and oxidative stress in neurodegenerative diseases. Nature 443 (2006): 787-795; Jorge J. PALOP, Jeannie Chin and Lennart Mucke. A network dysfunction perspective on neurodegenerative diseases. Nature 443 (2006): 768-773; David C. RUBINSZTEIN. The roles of intracellular protein-degradation pathways in neurodegeneration. Nature 443 (2006): 780-786].

The present invention is concerned primarily with the treatment of a particular class of neurodegenerative disease, namely, neurodegenerative dementias, among which Alzheimer (or Alzheimer's) disease (AD) is the most prevalent. However, it is understood that according to the previous paragraph, treatments that are disclosed here might be applicable to other neurodegenerative diseases as well.

Dementia is a clinical diagnosis that is based on evidence of cognitive dysfunction in both the patient's history and in successive mental status examinations. The diagnosis is made when there is impairment in two or more of the following: learning and retaining newly acquired information (episodic declarative memory); handling complex tasks and reasoning abilities (executive cognitive functions); visuospatial ability and geographic orientation; and language functions. The diagnosis may be made after excluding potentially treatable disorders that may otherwise contribute to cognitive impairment, such as depression, vitamin deficiencies, hypothyroidism, tumor, subdural hematomas, central nervous system infection, a cognitive disorder related to human immunodeficiency virus infection, adverse effects of prescribed medications, and substance abuse [McKHANN G, Drachman D, Folstein M, Katzman R, Price D, Stadlan E M. Clinical diagnosis of Alzheimer's disease: report of the NINCDS-ADRDA Work Group under the auspices of Department of Health and Human Services Task Force on Alzheimer's Disease. Neurology 34(7, 1984):939-44; David S. KNOPMAN. Alzheimer's Disease and other dementias. Chapter 409 (pp. 2274-2283) In: Goldman's Cecil Medicine, 24th Edn. (Lee Goldman and Andrew I. Schafer, Eds.). Philadelphia: Elsevier-Saunders, 2012; THOMPSON S B. Alzheimers Disease Comprehensive Review of Aetiology, Diagnosis, Assessment Recommendations and Treatment. Webmed Central AGING 2011; 2(3): WMC001681, pp. 1-42].

Dementia prevalence increases with age, from 5% of those aged 71-79 years to 37% of those aged 90 and older. However, despite their prevalence in old age, dementias such as Alzheimer's disease are not an integral part of the aging process [NELSON P T, Head E, Schmitt F A, Davis P R, Neltner J H, Jicha G A, Abner E L, Smith C D, Van Eldik Li, Kryscio R J, Scheff S W. Alzheimer's disease is not "brain aging": neuropathological, genetic, and epidemiological human studies. Acta Neuropathol 121(5, 2011):571-87]. Genetics plays a role in early-onset AD (less than 1% of cases). The most powerful genetic risk factor for the more common forms of AD is the APOE e4 gene, one or more copies of which are carried by 60% of AD patients in some populations. Otherwise, the risk of AD may be increased by a low level of education, severe head injury, cerebrovascular disease, diabetes and obesity.

In the United States, the average annual cost of caring for a person with dementia in 2010 was $60,090. The total estimated worldwide annual costs of dementia were $604 billion in 2010, which exceeded the entire gross national product of Indonesia, Belgium, or Sweden [PLASSMAN B L, Langa K M, Fisher G G, Heeringa S G, Weir D R, Ofstedal M B, Burke J R, Hurd M D, Potter G G, Rodgers W L, Steffens D C, Willis R J, Wallace R B. Prevalence of dementia in the United States: the aging, demographics, and memory study. Neuroepidemiology 29(1-2, 2007):125-32; Anders WIMO and Martin Prince. Alzheimer's Disease International World Alzheimer Report 2010. The Global Economic Impact of Dementia. pp. 1-56. Alzheimer's Disease International (ADI). 64 Great Suffolk Street London SE 1 0BL, UK].

The principal diseases that cause dementia are three neurodegenerative diseases (Alzheimer's disease, Lewy body disease, and frontotemporal lobar degeneration) and cerebrovascular disease. In the United States, Alzheimer's disease accounts for approximately 70% of cases of dementia, and vascular dementia accounts for 17% of cases. Lewy body dementia and frontotemporal lobar dementia account for the remaining 13% of cases, along with less common causes (e.g., alcoholic/toxic dementia, traumatic brain injury, normal-pressure hydrocephalus, Parkinson's dementia, Creutzfeldt-Jakob disease, and undetermined etiology). In absolute numbers, 5.4 million Americans are currently living with Alzheimer's disease, and Lewy Body dementia affects 1.3 million Americans.

Patients with each type of dementia exhibit certain typical symptoms. In Alzheimer's disease, anterograde amnesia is a dominant symptom—loss of the ability to create new memories of events occurring after the onset of the disease. Dementia with Lewy bodies is characterized by parkinsonism, visual hallucinations, and a rapid-eye-movement sleep disorder. Frontotemporal lobar degeneration is characterized by prominent behavioral and personality changes or by prominent language difficulties early in the course of the disease. Cerebrovascular dementia, which may be a sequela of atherosclerosis, is due to one or more cerebral infarctions (ischemic strokes) in brain locations that are responsible for the cognitive deficits. The simultaneous presence of Alzheimer's disease with vascular dementia is common, and it may be difficult to distinguish these two dementia on the basis of symptoms alone.

Hour-to-hour and day-to-day changes in cognition may also be exhibited by individuals with dementia. Thus, caregivers of patients with dementia often notice that the patient may be confused and incoherent at one time, and only a few hours later, or the next day, the patient is alert and coherent. The time-course and situational antecedent of those so-called cognitive fluctuations may also be helpful in distinguishing one form of dementia from the others, using clinical scales have been developed to analyze such fluctuations (Clinician Assessment of Fluctuation, One Day Fluctuation Assessment Scale, Mayo Fluctuation Questionnaire). Dementia with Lewy bodies is associated with transient and spontaneous episodes of confusion and an inability to engage in meaningful cognitive activity, followed by reversion to a near normal level of function, often within hours. In contrast, cognitive fluctuations in Alzheimer's disease are often elicited by situations in which an underlying cognitive impairment manifests itself, typically as repetitiveness in conversation, forgetfulness in relation to a recent task or event, or other behavioral consequences of poor memory. In addition to this situational triggering aspect of a cognitive fluctuation in patients with Alzheimer's disease, the confusion is often a more enduring state shift (good days/bad days), rather than an hour-to-hour shift.

The mechanism of cognitive fluctuation is unknown, either for the hour-to-hour type that is common in dementia with Lewy bodies, or the day-to-day type that is not uncommon among Alzheimer patients. However, the mechanism is clearly different than the ones involved in circadian phenomena, such as "sundowning," because the cognitive fluctuation need not occur around a particular time of day. Whatever the mechanism of cognitive fluctuations, it would be very beneficial to be able to prevent or reverse them, if only as a prophylactic or symptomatic treatment, so as to spare the patient and caregiver of the stress associated with fluctuating cognitive impairment as it relates to impairment of activities of daily living [Jorge J. PALOP, Jeannie Chin and Lennart Mucke. A network dysfunction perspective on neurodegenerative diseases. Nature 443(7113, 2006):768-73; WALKER M P, Ayre G A, Cummings J L, Wesnes K, McKeith I G, O'Brien J T, Ballard C G. The Clinician Assessment of Fluctuation and the One Day Fluctuation Assessment Scale. Two methods to assess fluctuating confusion in dementia. Br J Psychiatry 177 (2000):252-6; BRADSHAW J, Saling M, Hopwood M, Anderson V, Brodtmann A. Fluctuating cognition in dementia with Lewy bodies and Alzheimer's disease is qualitatively distinct. J Neurol Neurosurg Psychiatry 75(3, 2004):382-7; BALLARD C, Walker M, O'Brien J, Rowan E, McKeith I. The characterisation and impact of 'fluctuating' cognition in dementia with Lewy bodies and Alzheimer's disease. Int J Geriatr Psychiatry 16(5, 2001):494-8; CUMMINGS J L. Fluctuations in cognitive function in dementia with Lewy bodies. Lancet Neurol 3(5, 2004):266; David R. LEE, John-Paul Taylor, Alan J. Thomas. Assessment of cognitive fluctuation in dementia: a systematic review of the literature. International Journal of Geriatric Psychiatry 27(10, 2012): 989-998; BACHMAN D, Rabins P. "Sundowning" and other temporally associated agitation states in dementia patients. Annu Rev Med 57 (2006):499-511].

As described above, dementia is a clinical diagnosis that is based on evidence of cognitive dysfunction in both the patient's history and in successive mental status examinations. With the ability to better stage the progression of dementia, treatment might be justified at stages prior to actual onset of the dementia. In particular, the present invention might best be used early in the course of the disease progression, such that treatment could be directed to slowing, stopping, or even reversing the pathophysiological processes underlying the dementia. Thus, the present invention contemplates treatments even when the patient exhibits prodromal symptoms or when the patient has been diagnosed with mild cognitive impairment (MCI) [DeCARLI C. Mild cognitive impairment: prevalence, prognosis, aetiology, and treatment. Lancet Neurol 2(1, 2003):15-21; MAYEUX R. Clinical practice. Early Alzheimer's disease. N Engl J Med 362(23, 2010):2194-2201; WILSON R S, Leurgans S E, Boyle P A, Bennett D A. Cognitive decline in prodromal Alzheimer disease and mild cognitive impairment. Arch Neurol 68(3, 2011):351-356].

Early staging of the patient's disease progression makes use of biomarkers, which are cognitive, physiological, biochemical, and anatomical variables that can be measured in a patient that indicate the progression of a dementia such as AD. The most commonly measured biomarkers for AD include decreased Aβ42 in the cerebrospinal fluid (CSF), increased CSF tau, decreased fluorodeoxyglucose uptake on PET (FDG-PET), PET amyloid imaging, and structural MRI measures of cerebral atrophy. Use of biomarkers to stage AD has developed to the point that biomarkers can be used with revised criteria for diagnosing the disease [MASDEU J C, Kreisl W C, Berman K F. The neurobiology of Alzheimer disease defined by neuroimaging. Curr Opin Neurol 25(4, 2012):410-420; DUBOIS B, Feldman H H, Jacova C, Dekosky S T, Barberger-Gateau P, Cummings J, Delacourte A, Galasko D, Gauthier S, Jicha G, Meguro K, O'brien J, Pasquier F, Robert P, Rossor M, Salloway S, Stern Y, Visser P J, Scheltens P. Research criteria for the diagnosis of Alzheimer's disease: revising the NINCDS-ADRDA criteria. Lancet Neurol 6(8, 2007):734-46; GAUTHIER S, Dubois B, Feldman H, Scheltens P. Revised research diagnostic criteria for Alzheimer's disease. Lancet Neurol 7 (8, 2008): 668-670].

In the remainder of this background section, current methods of treating AD are described. As summarized here, they include methods to treat cognitive symptoms of AD patients, as well as methods that are intended to treat the underlying pathophysiological progression of AD. Because the methods described in the publications cited below have not been demonstrated to exhibit more than very modest success in treating only symptoms of AD, and no method is known to stop the progression of AD, additional methods are clearly needed, which motivates the invention that is disclosed here. Because the disclosure involves vagus nerve stimulation, the effect of stimulation on the patient's locus ceruleus, and consequences of that effect, the literature relevant to those subjects is emphasized in what follows.

Before the currently favored amyloid cascade hypothesis of AD (and subsequent variants of that hypothesis), the focus of AD research was the search for a clearly defined neurochemical abnormality in AD patients, which would provide the basis for the development of rational therapeutic interventions that are analogous to levodopa treatment of Parkinson's disease. This led to the cholinergic hypothesis of Alzheimer's disease, which proposed that degeneration of cholinergic neurons in the basal forebrain and the associated loss of cholinergic neurotransmission in the cerebral cortex and other areas contributed significantly to the deterioration in cognitive function seen in patients with Alzheimer's disease. The symptomatic drug treatments that arose from that research are currently the mainstay of AD treatment, even though their effectiveness is very modest, and no drug delays the progression of the disease. Approved drugs for the symptomatic treatment of AD modulate neurotransmitters—either acetylcholine or glutamate: cholinesterase inhibitors (tacrine, rivastigmine, galantamine and donepezil) and partial N-methyl-D-aspartate antagonists (memantine) [FRANCIS P T, Ramírez M J, Lai M K. Neurochemical basis for symptomatic treatment of Alzheimer's disease. Neuropharmacology 59(4-5, 2010):221-229; FRANCIS P T, Palmer A M, Snape M, Wilcock G K. The cholinergic hypothesis of Alzheimer's disease: a review of progress. J Neurol Neurosurg Psychiatry 66(2, 1999):137-47; MESULAM M. The cholinergic lesion of Alzheimer's disease: pivotal factor or side show? Learn Mem 11(1, 2004):43-49].

The symptomatic treatment of AD by modulating neurotransmitters other than acetylcholine or glutamate has also been considered. One such neurotransmitter is norepinephrine (noradrenaline), which in the brain is principally synthesized in the locus ceruleus. A rationale for therapeutic modulation of norepinephrine levels has been that in AD, there is loss of noradrenergic neurons in the locus ceruleus, and the treatment would compensate for that loss [HAGLUND M, Sjöbeck M, Englund E. Locus ceruleus degeneration is ubiquitous in Alzheimer's disease: possible implications for diagnosis and treatment. Neuropathology 26(6, 2006):528-32; SAMUELS E R, Szabadi E. Functional neuroanatomy of the noradrenergic locus coeruleus: its roles in the regulation of arousal and autonomic function part II: physiological and pharmacological manipulations and pathological alterations of locus coeruleus activity in humans. Curr Neuropharmacol 6(3, 2008):254-85; Patricia SZOT. Common factors among Alzheimer's disease, Parkinson's disease, and epilepsy: Possible role of the noradrenergic nervous system. Epilepsia 53(Suppl. 1, 2012):61-66].

Accordingly, several investigators proposed to increase brain norepinephrine as a therapy for AD patients [E M VAZEY, V K Hinson, A C Granholm, M A Eckert, G A Jones. Norepinephrine in Neurodegeneration: A Coerulean Target. J Alzheimers Dis Parkinsonism 2(2, 2012): 1000e114, pp. 1-3]. Administration of norepinephrine itself is not feasible as a method for increasing its levels in the central nervous system because norepinephrine, as with other catecholamines, cannot cross the blood-brain barrier. Many other drugs such as amphetamines and methylphenidate can increase norepinephrine brain levels, but they affect other neurotransmitter systems as well and have significant side effects. Consequently, less direct methods have been used or suggested as ways to increase norepinephrine levels in the central nervous system, or to activate adrenergic signaling. They include the use of special drugs that mimic norepinephrine, that serve as precursors of norepinephrine, that block the reuptake of norepinephrine, and that serve as adrenoceptor antagonists that enhances norepinephrine release [MISSONNIER P, Ragot R, Derouesné C, Guez D, Renault B. Automatic attentional shifts induced by a noradrenergic drug in Alzheimer's disease: evidence from evoked potentials. Int J Psychophysiol 33(3, 1999): 243-51; FRIEDMAN J I, Adler D N, Davis K L. The role of norepinephrine in the pathophysiology of cognitive disorders: potential applications to the treatment of cognitive dysfunction in schizophrenia and Alzheimer's disease. Biol Psychiatry. 46(9, 1999):1243-52; KALININ S, Polak P E, Lin S X, Sakharkar A J, Pandey S C, Feinstein D L. The noradrenaline precursor L-DOPS reduces pathology in a mouse model of Alzheimer's disease. Neurobiol Aging 33(8, 2012):1651-1663; MOHS, R. C., Shiovitz, T. M., Tariot, P. N., Porsteinsson, A. P., Baker, K. D., Feldman, P. D., 2009. Atomoxetine augmentation of cholinesterase inhibitor therapy in patients with Alzheimer disease: 6-month, randomized, double-blind, placebo-controlled, parallel-trial study. Am. J. Geriatr. Psychiatry 17, 752-759; SCULLION G A, Kendall D A, Marsden C A, Sunter D, Pardon M C. Chronic treatment with the a2-adrenoceptor antagonist fluparoxan prevents age-related deficits in spatial working memory in APPxPS1 transgenic mice without altering β-amyloid plaque load or astrocytosis. Neuropharmacology 60(2-3, 2011):223-34]. Other agents that are thought to alter norepinephrine levels, via locus ceruleus activity, include chronic stress, chronic opiate treatment, and anti-depressant treatment [NESTLER E J, Alreja M, Aghajanian G K. Molecular control of locus coeruleus neurotransmission. Biol Psychiatry 46(9, 1999):1131-1139; SAMUELS, E. R., and Szabadi, E. Functional neuroanatomy of the noradrenergic locus coeruleus: its roles in the regulation of arousal and autonomic function part II: physiological and pharmacological manipulations and pathological alterations of locus coeruleus activity in humans. Curr. Neuropharmacol. 6 (2008), 254-285].

However, for several reasons, it is not settled that a pharmacologically-induced increase of norepinephrine, or increased signaling through the adrenergic receptors in the central nervous system, will substantially benefit AD patients. First, in patients with AD, clonidine (a centrally acting alpha2 adrenergic agonist) was reported to have no effect on cognitive functions, and may even impair sustained attention and memory. Another putative alpha2-adrenoceptor agonist, guanfacine, has consistently been shown to be without effect on cognitive functions. Thus, administration of clonidine or guanfacine does not appear to provide any consistent improvement in cognitive functions, either in normal subjects or in patients with AD or other cognitive impairments. On the other hand, the alpha2-adrenoceptor antagonist, idazoxan, improved planning, sustained attention, verbal fluency, and episodic memory but impaired spatial working memory in patients with dementia of the frontal type [MARIEN M R, Colpaert F C, Rosenquist A C. Noradrenergic mechanisms in neurodegenerative diseases: a theory. Brain Res Brain Res Rev 45(1, 2004):38-78].

Second, norepinephrine significantly worsens agitation and anxiety in AD patients, such that any potential benefits of increased norepinephrine levels may be offset by behavioral side effects, as well as cardiovascular side effects [HERRMANN N, Lanctôt K L, Khan L R. The role of norepinephrine in the behavioral and psychological symptoms of dementia. J Neuropsychiatry Clin Neurosci 16(3, 2004):261-76; PESKIND, E. R., Tsuang, D. W., Bonner, L. T., Pascualy, M., Riekse, R. G., Snowden, M. B., Thomas, R., Raskind, M. A. Propranolol for disruptive behaviors in nursing home residents with probable or possible Alzheimer disease: a placebo-controlled study. Alzheimer Dis. Assoc. Disord. 19 (2005): 23-28].

Third, loss of locus ceruleus cells in AD may lead to compensatory production of norepinephrine in other cells, such that there may actually be an increase in norepinephrine levels in some AD patients [Fitzgerald P J. Is elevated norepinephrine an etiological factor in some cases of Alzheimer's disease? Curr Alzheimer Res 7(6, 2010):506-16; ELROD R, Peskind E R, DiGiacomo L, Brodkin K I, Veith R C, Raskind M A. Effects of Alzheimer's disease severity on cerebrospinal fluid norepinephrine concentration. Am J Psychiatry 154(1, 1997):25-30].

Even if there is a decrease in overall brain norepinephrine levels in AD, this decrease does not necessarily occur uniformly among brain regions that are modulated by the locus ceruleus, and patterns of compensatory receptor alterations may also be complicated, with selective decreases and increases of noradrenergic receptors subtypes in different regions of the brain [HOOGENDIJK W J, Feenstra M G, Botterblom M H, Gilhuis J, Sommer I E, Kamphorst W, Eikelenboom P, Swaab D F. Increased activity of surviving locus ceruleus neurons in Alzheimer's disease. Ann Neurol 45(1, 1999):82-91; SZOT P, White S S, Greenup J L, Leverenz J B, Peskind E R, Raskind M A. Compensatory changes in the noradrenergic nervous system in the locus coeruleus and hippocampus of postmortem subjects with Alzheimer's disease and dementia with Lewy Bodies. J Neurosci 26 (2006):467-478; SZOT P, White S S, Greenup J L, Leverenz J B, Peskind E R, Raskind M A. Changes in adrenoreceptors in the prefrontal cortex of subjects with dementia: evidence of compensatory changes. Neuroscience 146 (2007):471-480].

Therefore, what is needed is not a pharmacological method that increases norepinephrine levels indiscriminately throughout the central nervous system of AD patients, but rather a method that can selectively increase (or decrease) the norepinephrine levels only where it is needed. This is true whether the increase is intended to improve cognition or whether the increase in norepinephrine levels is intended to prevent, delay or antagonize pathological biochemical changes that occur in the brains of AD patients [COUNTS S E, Mufson E J. Noradrenaline activation of neurotrophic pathways protects against neuronal amyloid toxicity. J Neurochem 113(3, 2010):649-60; WENK G L, McGann K, Hauss-Wegrzyniak B, Rosi S. The toxicity of tumor necrosis factor-alpha upon cholinergic neurons within the nucleus basalis and the role of norepinephrine in the regulation of inflammation: implications for Alzheimer's disease. Neuroscience 121(3, 2003):719-29; KALININ S, Gavrilyuk V, Polak P E, Vasser R, Zhao J, Heneka M T, Feinstein D L. Noradrenaline deficiency in brain increases beta-amyloid plaque burden in an animal model of Alzheimer's disease. Neurobiol Aging 28(8, 2007):1206-1214; HENEKA M T, Ramanathan M, Jacobs A H, Dumitrescu-Ozimek L, Bilkei-Gorzo A, Debeir T, Sastre M, Galldiks N, Zimmer A, Hoehn M, Heiss W D, Klockgether T, Staufenbiel M. Locus ceruleus degeneration promotes Alzheimer pathogenesis in amyloid precursor protein 23 transgenic mice. J. Neurosci. 26(5, 2006):1343-54; HENEKA M T, Nadrigny F, Regen T, Martinez-Hernandez A, Dumitrescu-Ozimek L, Terwel D, Jardanhazi-Kurutz D, Walter J, Kirchhoff F, Hanisch U K, Kummer M P. Locus ceruleus controls Alzheimer's disease pathology by modulating microglial functions through norepinephrine. Proc Natl Acad Sci USA. 107(13, 2010):6058-6063; JARDANHAZI-KURUTZ D, Kummer M P, Terwel D, Vogel K, Thiele A, Heneka M T. Distinct adrenergic system changes and neuroinflammation in response to induced locus ceruleus degeneration in APP/PS1 transgenic mice. Neuroscience 176 (2011):396-407; YANG J H, Lee E O, Kim S E, Suh Y H, Chong Y H. Norepinephrine differentially modulates the innate inflammatory response provoked by amyloid-R peptide via action at β-adrenoceptors and activation of cAMP/PKA pathway in human THP-1 macrophages. Exp Neurol 236(2, 2012):199-206; KONG Y, Ruan L, Qian L, Liu X, Le Y. Norepinephrine promotes microglia to uptake and degrade amyloid beta peptide through upregulation of mouse formyl peptide receptor 2 and induction of insulin-degrading enzyme. J Neurosci 30(35, 2012):11848-11857; KALININ S, Polak P E, Lin S X, Sakharkar A J, Pandey S C, Feinstein D L. The noradrenaline precursor L-DOPS reduces pathology in a mouse model of Alzheimer's disease. Neurobiol Aging 33(8, 2012):1651-1663; HAMMERSCHMIDT T, Kummer M P, Terwel D, Martinez A, Gorji A, Pape H C, Rommelfanger K S, Schroeder J P, Stoll M, Schultze J, Weinshenker D, Heneka M T. Selective Loss of Noradrenaline Exacerbates Early Cognitive Dysfunction and Synaptic Deficits in APP/PS1 Mice. Biol Psychiatry. 2012 Aug. 9. Epub ahead of print, pp. 1-10; O'DONNELL J, Zeppenfeld D, McConnell E, Pena S, Nedergaard M. Norepinephrine: A Neuromodulator That Boosts the Function of Multiple Cell Types to Optimize CNS Performance. Neurochem Res. 2012 Jun. 21. (Epub ahead of print}, pp. 1-17]. Psychotropic medications are also used in conjunction with the neurotransmitter modulators to treat secondary symptoms of AD such as depression, agitation, and sleep disorders [Julius POPP and Sonke Arlt. Pharmacological treatment of dementia and mild cognitive impairment due to Alzheimer's disease. Current Opinion in Psychiatry 24 (2011):556-561; Fadi MASSOUD and Gabriel C Leger. Pharmacological treatment of Alzheimer disease. Can J. Psychiatry. 56(10, 2011):579-588; Carl H. SADOWSKY and James E. Galvin. Guidelines for the management of cognitive and behavioral problems in dementia. J Am Board Fam Med 25 (2012):350-366].

Therapies based on nutrition, lifestyle modification, herbal or dietary supplements (e.g., Huperzine A), brain exercises, and other integrative methods have also been proposed [Dharma Singh KHALSA. Alzheimer Disease. pp. 78-90 (Chapter 9) In: Integrative Medicine, 3rd Ed. (David Rakel, ed.) Philadelphia, Pa.: Elsevier Saunders, 2012; Clive BALLARD, Zunera Khan, Hannah Clack, and Anne Corbett. Nonpharmacological treatment of Alzheimer disease. The Canadian Journal of Psychiatry 56(10, 2011): 589-595; DAVIGLUS M L, Bell C C, Berrettini W, Bowen P E, Connolly E S, Cox N J, Dunbar-Jacob J M, Granieri E C, Hunt G, McGarry K, Patel D, Potosky A L, Sanders-Bush E, Silberberg D, Trevisan M. NIH State-of-the-Science Conference Statement: Preventing Alzheimer's Disease and Cognitive Decline. NIH Consens State Sci Statements 27(4, 2010), pp. 1-121].

Therapies directed to modifying AD progression itself are considered investigational. These include treatment of the intense inflammation that occurs in the brains of patients with AD, estrogen therapy, use of free-radical scavengers, therapies designed to decrease toxic amyloid fragments in the brain (vaccination, anti-amyloid antibodies, selective amyloid-lowering agents, chelating agents to prevent amyloid polymerization, brain shunting to improve removal of amyloid, and beta-secretase inhibitors to prevent generation of the A-beta amyloid fragment), and agents that may prevent or reverse excess tau phosphorylation and thereby diminish formation of neurofibrillary tangles. Some agents, such as retinoids, may target multiple aspects of AD pathogenesis [TAYEB H O, Yang H D, Price B H, Tarazi F I. Pharmacotherapies for Alzheimer's disease: beyond cholinesterase inhibitors. Pharmacol Ther 134(1, 2012):8-25; LEMER A J, Gustaw-Rothenberg K, Smyth S, Casadesus G. Retinoids for treatment of Alzheimer's disease. Biofactors 38(2, 2012):84-89; KURZ A, Perneczky R. Novel insights for the treatment of Alzheimer's disease. Prog Neuropsychopharmacol Biol Psychiatry 35(2, 2011):373-379; MINATI L, Edginton T, Bruzzone M G, Giaccone G. Current concepts in Alzheimer's disease: a multidisciplinary review. Am J Alzheimers Dis Other Demen 24(2, 2009):95-121].

However, it is increasingly recognized that a single target or pathogenic pathway for the treatment of AD is unlikely to be identified. The best strategy is thought to be a multi-target therapy that includes multiple types of treatments [MANGIALASCHE F, Solomon A, Winblad B, Mecocci P, Kivipelto M. Alzheimer disease: clinical trials and drug development. Lancet Neurol 9(7, 2010):702-716]. Targets in that multi-target approach will include inflammatory pathways, and several therapeutic agents have been proposed to target them—nonsteroidal anti-inflammatory drugs, statins, RAGE antagonists and antioxidants [STUCHBURY G, Münch G. Alzheimer associated inflammation, potential drug targets and future therapies. J Neural Transm. 2005 March; 112(3): 429-53 Joseph BUTCHART and Clive Holmes. Systemic and Central Immunity in Alzheimer's Disease: Therapeutic Implications. CNS Neuroscience & Therapeutics 18 (2012): 64-76]. Another such agent, Etanercept, targets TNF-alpha, but its use has the disadvantage that because it does not pass the blood-brain barrier (BBB), its administration is via a painful spinal route or via an experimental method to get through the BBB [U.S. Pat. No. 7,640,062, entitled Methods and systems for management of alzheimer's disease, to SHALEV]. One TNF-inhibitor that does not have this disadvantage is thalidomide [Tweedie D, Sambamurti K, Greig N H: TNF-alpha Inhibition as a Treatment Strategy for Neurodegenerative Disorders: New Drug Candidates and Targets. Curr Alzheimer Res 2007, 4(4):375-8]. However, thalidomide is well known by the public to cause birth defects, and in a small trial, its use did not appear to improve cognition in AD patients [Peggy PECK. IADRD: Pilot Study of Thalidomide for Alzheimer's Disease Fails to Detect Cognitive Benefit but Finds Effect on TNF-alpha. Doctor's Guide Global Edition, Jul. 26, 2002].

Various devices have been proposed to restore or enhance cognition, including cognition of AD patients [Mijail Demian SERRUYA and Michael J. Kahana. Techniques and devices to restore cognition. Behav Brain Res 192(2, 2008): 149-165]. Deep brain electrical stimulation has been generally unsuccessful or counterproductive in attempting to enhance the memory of AD patients. However, improved verbal recall has been observed in one case study in which deep-brain stimulation of the hypothalamus and fornix was used to treat morbid obesity [HAMANI C, McAndrews M P, Cohn M, Oh M, Zumsteg D, Shapiro C M, Wennberg R A, Lozano A M. Memory enhancement induced by hypothalamic/fornix deep brain stimulation. Ann Neurol 63 (2008):119-23; Adrian W. LAXTON and Andres M. Lozano. Deep brain stimulation for the treatment of Alzheimer disease and dementias. World Neurosurg. (2012), pp. 1-8]. Entorhinal, but not hippocampal, deep brain stimulation has also been found to improve memory used in spatial navigation. Authors of that investigation suggest that in using neuroprosthetic devices for purposes of cognitive enhancement, stimulation may not need to be applied continuously, but instead only when patients are attempting to learn important information. They also suggest that resetting of the phase of the theta rhythm in the EEG (3-8 Hz) improves memory performance, as has been observed in animal experiments [Nanthia SUTHANA, Zulfi Haneef, John Stern, Roy Mukamel, Eric Behnke, Barbara Knowlton and Itzhak Fried. Memory enhancement and deep-brain stimulation of the entorhinal area. N Engl J Med 366 (2012):502-10; LEMON N, Aydin-Abidin S, Funke K, Manahan-Vaughan D. Locus coeruleus activation facilitates memory encoding and induces hippocampal LTD that depends on beta-adrenergic receptor activation. Cereb Cortex 19(12, 2009):2827-37].

Magnetic stimulation of AD patients has also been performed, but its use has been intended only to affect cognitive skills and only using transcranial magnetic stimulation [Mamede de CARVALHO, Alexandre de Mendonça, Pedro C. Miranda, Carlos Garcia and Maria Lourdes Sales Luís. Magnetic stimulation in Alzheimer's disease. Journal of Neurology 244 (1997, 5): 304-307; COTELLI M, Manenti R, Cappa S F, Zanetti O, Miniussi C. Transcranial magnetic stimulation improves naming in Alzheimer disease patients at different stages of cognitive decline. Eur J. Neurol. 15(12, 2008):1286-92; GUSE B, Falkai P, Wobrock T. Cognitive effects of high-frequency repetitive transcranial magnetic stimulation: a systematic review. J Neural Transm. 117(1, 2010):105-22; Raffaele NARDONE, Jurgen Bergmann, Monica Christova, Francesca Caleri, Frediano Tezzon, Gunther Ladurner, Eugen Trinka and Stefan Golaszewski. Effect of transcranial brain stimulation for the treatment of Alzheimer disease: A review. International Journal of Alzheimer's Disease 2012, Article ID 687909: pp. 1-5; Raffaele NARDONE, Stefan Golaszewski, Gunther Ladurner, Frediano Tezzon, and Eugen Trinka. A Review of Transcranial Magnetic Stimulation in the in vivo Functional Evaluation of Central Cholinergic Circuits in Dementia. Dement Geriatr Cogn Disord 32 (2011):18-25].

A method of using vagal nerve stimulation to treat AD symptoms was disclosed in U.S. Pat. No. 5,269,303, entitled Treatment of dementia by nerve stimulation, to WERNICKE et al. It is directed to "a symptom of dementia" which was described as being either paroxysmal activity exhibited in the patient's EEG or the level of alertness of the patient, but not to cognition per se.

In 2002, it was reported that electrical stimulation of the vagus nerve has a beneficial effect on cognition in patients with AD [SJOGREN M J, Hellström P T, Jonsson M A, Runnerstam M, Silander H C, Ben-Menachem E. Cognition-enhancing effect of vagus nerve stimulation in patients with Alzheimer's disease: a pilot study. J Clin Psychiatry 63(11, 2002):972-80]. The rationale for that trial was that vagus nerve stimulation had previously been found to enhance the cognitive abilities of patients that were undergoing vagus nerve stimulation for other conditions such as epilepsy and depression, as well as enhanced cognitive abilities observed in animal studies. Results concerning the AD patients' improved cognitive abilities over a longer period of time, along with improvement in tau protein of cerebrospinal fluid, were subsequently reported [MERRILL C A, Jonsson M A, Minthon L, Ejnell H, C-son Silander H, Blennow K, Karlsson M, Nordlund A, Rolstad S, Warkentin S, Ben-Menachem E, Sjögren M J. Vagus nerve stimulation in patients with Alzheimer's disease: Additional follow-up results of a pilot study through 1 year. J Clin Psychiatry. 2006 August; 67(8):1171-8]. Those results were immediately greeted with skepticism, particularly the purported changes in tau protein, because there was no control group and the number of patients was small [Theresa DEFINO. Symptoms stable in AD patients who underwent vagus nerve stimulation. Neurology Today 6(21, 2006):14-15].

Stimulation of the vagus nerve to treat at least the symptomatic cognitive aspects of dementia might be more effective than stimulation of nerves found in locations such as the spine, forehead, and earlobes [CAMERON M H, Lonergan E, Lee H. Transcutaneous Electrical Nerve Stimulation (TENS) for dementia. Cochrane Database of Systematic Reviews 2003, Issue 3. Art. No.: CD004032. (2009 update); Erik J. A. SCHERDER, Marijn W. Luijpen, and Koene R. A. van Dijk. Activation of the dorsal raphe nucleus and locus coeruleus by transcutaneous electrical nerve stimulation in Alzheimer's disease: a reconsideration of stimulation-parameters derived from animal studies. Chinese Journal of Physiology 46(4, 2003): 143-150]. However, BOON and colleagues dispute the claim that vagus nerve stimulation with prevailing stimulation parameters can enhance even the cognitive abilities of human patients, although they do conclude that such stimulation can improve cognition in animal models [Paul BOON, Ine Moors, Veerle De Herdt, Kristl Vonck. Vagus nerve stimulation and cognition. Seizure 15 (2006), 259-263]. In fact, in humans, vagus nerve stimulation impairs cognitive flexibility and creative thinking [GHACIBEH G A, Shenker J I, Shenal B, Uthman B M, Heilman K M. Effect of vagus nerve stimulation on creativity and cognitive flexibility. Epilepsy Behav 8(4, 2006):720-725]. Furthermore, it has no effect on learning, but it might enhance memory consolidation, which leads to improved retention [GHACIBEH G A, Shenker J I, Shenal B, Uthman B M, Heilman K M. The influence of vagus nerve stimulation on memory. Cogn Behav Neurol 19(3, 2006):119-22; CLARK K B, Naritoku D K, Smith D C, Browning R A, Jensen R A. Enhanced recognition memory following vagus nerve stimulation in human subjects. Nature Neurosci 2 (1999):94-98]. Among different types of memories, vagus nerve stimulation is reported to improve only verbal recognition memory [McGLONE J, Valdivia I, Penner M, Williams J, Sadler R M, Clarke D B. Quality of life and memory after vagus nerve stimulator implantation for epilepsy. Can J Neurol Sci 35(3, 2008):287-96]. However, most such investigations have been performed on patients with electrodes implanted to control epilepsy, so patients with Alzheimer's disease were not included in the studies.

The effects of vagus nerve stimulation on the cognition of animal models are given in experiments described in the following publications. The animal experiments show generally that it may be possible to promote cognition using vagus nerve stimulation, which suggests that failure in the above-mentioned human experiments might be attributable to using stimulation parameters that treat epilepsy or depression, instead of parameters that preferentially enhance cognition. Vagus nerve stimulation was shown to activate the locus ceruleus and to increase norepinephrine output into the basolateral amygdala and hippocampus in rats [NARITOKU D K, Terry W J, Helfert R H. Regional induction of fos immunoreactivity in the brain by anticonvulsant stimulation of the vagus nerve. Epilepsy Res 22(1, 1995):53-62; HASSERT D L, Miyashita T, Williams C L. The effects of peripheral vagal nerve stimulation at a memory-modulating intensity on norepinephrine output in the basolateral amygdala. Behav Neurosci 118(1, 2004):79-88; CHEN C C, Williams C L. Interactions between epinephrine, ascending vagal fibers, and central noradrenergic systems in modulating memory for emotionally arousing events. Front Behav Neurosci 6:35. Epub 2012 Jun. 28, pp. 1-20].

In a rat model of traumatic brain injury, it was shown that vagus nerve stimulation facilitated both the rate of recovery and the extent of motor and cognitive recovery [SMITH D C, Modglin A A, Roosevelt R W, Neese S L, Jensen R A, Browning R A, et al. Electrical stimulation of the vagus nerve enhances cognitive and motor recovery following moderate fluid percussion injury in the rat. J Neurotrauma 22(12, 2005):1485-1502]. Electrical stimulation of the vagus nerve (VNS) delivered at a moderate intensity following a learning experience enhances memory in laboratory rats, while VNS at lower or higher intensities has little or no effect, which appears to involve modulating synaptic plasticity in the hippocampus [ZUO Y, Smith D C, Jensen R A. Vagus nerve stimulation potentiates hippocampal LTP in freely moving rats. Physiol Behav 90(4, 2007):583-589]. More generally, vagus nerve stimulation modulates norepinephrine levels via effects on the locus ceruleus [DORR A E, Debonnel G. Effect of vagus nerve stimulation on serotonergic and noradrenergic transmission. J Pharmacol Exp Ther 318(2, 2006):890-898; MANTA S, Dong J, Debonnel G, Blier P. Enhancement of the function of rat serotonin and norepinephrine neurons by sustained vagus nerve stimulation. J Psychiatry Neurosci 34(4, 2009):272-80; SHEN H, Fuchino Y, Miyamoto D, Nomura H, Matsuki N. Vagus nerve stimulation enhances perforant path-CA3 synaptic transmission via the activation of β-adrenergic receptors and the locus coeruleus. Int J Neuropsychopharmacol 15(4, 2012):523-30].

Otherwise, the only mechanism by which vagus nerve stimulation has been suggested to affect synaptic activity (e.g., seizures) is via its effect on cerebral circulation [HENRY T R, Bakay R A, Pennell P B, Epstein C M, Votaw J R. Brain blood-flow alterations induced by therapeutic vagus nerve stimulation in partial epilepsy: II. prolonged effects at high and low levels of stimulation. Epilepsia 45(9, 2004):1064-1070].

In a commonly assigned, co-pending patent application (Publication US 20110152967, entitled Non-invasive treatment of neurodegenerative disease, to SIMON et al), Applicants disclosed six novel mechanisms by which stimulation of the vagus nerve may be used to treat the underlying pathophysiology of AD: (1) stimulate the vagus nerve in such a way as to enhance the availability or effectiveness of TGF-beta or other anti-inflammatory cytokines; (2) stimulate the vagus nerve in such a way as to enhance the availability or effectiveness of retinoic acid; (3) stimulate the vagus nerve in such a way as to promote the expression of the neurotrophic factors such as BDNF; (4) stimulate the vagus nerve to modulate the capacity of TNF-alpha to function as a gliotransmitter, including modulating the activity of the cells between which TNF-related gliotransmission occurs; (5) stimulate the vagus nerve to modulate the degradation of TNF-alpha, and/or modify the activity of existing TNF-alpha molecules as a pro-inflammatory mediator; and (6) stimulate the vagus nerve in such a way as to suppress the release or effectiveness of pro-inflammatory cytokines, through a mechanism that is distinct from the one proposed by TRACEY and colleagues. Thus, U.S. Pat. No. 6,610,713 and U.S. Pat. No. 6,838,471, entitled Inhibition of inflammatory cytokine production by cholinergic agonists and vagus nerve stimulation, to TRACEY, mention treatment of neurodegenerative diseases within a long list of diseases, in connection with the treatment of inflammation through stimulation of the vagus nerve. However, there is no mention or suggestion by TRACEY that his methods are intended to modulate the activity of anti-inflammatory cytokines, and in fact, his disclosures disclaim a role for antiinflammatory cytokines as mediators of inflammation through stimulation of the vagus nerve.

In the present application, additional methods and devices for the treatment or prevention of dementia, particularly Alzheimer's disease, are disclosed. The disclosed method does not increase norepinephrine levels indiscriminately throughout the CNS of AD patients, but instead preferentially increases the norepinephrine levels where it is needed, through selection of appropriate vagus nerve stimulation parameters, which may be adjusted on an individualized basis and on the basis of progression of the disease. The method prevents loss of the locus ceruleus and takes into account the existence of so-called resting state brain networks, particularly the default mode network and the ventral attention network. According to the invention, site-preferential modulation of norepinephrine levels by vagus nerve stimulation prevents, delays or antagonizes pathological biochemical changes that occur in the brains of AD patients and that lead to a loss of locus ceruleus cells. The stimulation may also enhance cognition, particularly in patients who are experiencing cognitive fluctuations.

SUMMARY OF THE INVENTION

The present invention involves devices and methods for the treatment of dementia, particularly Alzheimer's disease (AD). In certain aspects of the invention, a device or system comprises an energy source of magnetic and/or electrical energy that is transmitted non-invasively to, or in close proximity to, a selected nerve of the patient to temporarily stimulate, block and/or modulate the signals in the selected nerve. In preferred embodiments of the invention, the selected nerve is a vagus nerve.

A novel mechanism of action for benefiting AD patients, as well as patients with a precursor of AD (e.g., mild cognitive impairment), is based on the use of vagus nerve stimulation to induce the release of increased quantities of norepinephrine from projections of a patient's locus ceruleus. Norepinephrine is known to strongly suppress neuroinflammation in the central nervous system (CNS), and neuroinflammation directed against beta amyloid is a primary driver of neuronal loss in AD. According to the invention, normal levels of norepinephrine in the CNS maintain a tolerance of beta amyloid, which is also present in without AD.

However, in AD, the terminal fields of norepinephrine-releasing locus ceruleus cells that innervate those brain regions containing beta amyloid become damaged or destroyed, which then leads to the perikaryal loss of those locus ceruleus cells (Wallerian-like degeneration). Loss of locus ceruleus cells, and loss of the protective norepinephrine that they produce, triggers an increased release of pro-inflammatory cytokine and cytotoxic agents by microglial cells against decreasingly tolerated beta amyloid aggregates. This results in further damage to, and loss of, locus ceruleus terminal fields and the norepinephrine that they produce, as well as damage to or loss of other nearby nerve cells. The result is a vicious cycle in which both the protective locus ceruleus cells and beta amyloid-containing regions of the brain die. The present invention breaks this vicious cycle by using vagus nerve stimulation to induce the release of larger quantities of norepinephrine from projections of a patient's locus ceruleus. Thus, maintaining norepinephrine release as high as possible may disrupt this degenerative cycle by reducing neuroinflammation, thereby halting or slowing the progression of the disease and protecting the locus ceruleus itself.

The brain contains several neural networks that can be identified by brain imaging. One such network, the default mode network (DMN), is the principal region within which AD-related pathologies occur. The locus ceruleus is thought to project to all of the networks, including the DMN. Methods of the invention increase norepinephrine levels in the DMN, thereby reducing neuroinflammation there. Depending on the distribution of adrenergic receptor subtypes within the DMN, the vagus nerve stimulation may also deactivate the DMN. The locus ceruleus projects most strongly to a network known as the ventral attention network (VAN). Activation of the VAN via the locus ceruleus also deactivates neuronal activity in the DMN, which thereby reduces the pathological changes in the DMN that accompany a high level of neuronal activity there.

The progression of AD can be monitored through the use of biomarkers. A pre-symptomatic phase occurs first, in which individuals are cognitively normal but some have AD pathological changes. This is followed by a second prodromal phase of AD, commonly referred to as mild cognitive impairment (MCI). The final phase of AD is true dementia. Methods of the invention may be applied to patients in any of these stages. For most patients, the stimulation may be performed for 30 minutes, and the treatment is performed once a week for 12 weeks or longer, because the progression of the disease from prodrome to true dementia is a chronic situation. Alternatively, stimulation may be performed only when patients are attempting to learn important information. However, it is understood that parameters of the stimulation protocol may be varied in response to heterogeneity in the pathophysiology of patients. Different stimulation parameters may also be selected as the course of the patient's disease changes. In preferred embodiments, the disclosed methods and devices do not produce clinically significant side effects, such as agitation or anxiety, or changes in heart rate or blood pressure.

In one embodiment, the method of treatment includes positioning the coil of a magnetic stimulator non-invasively on or above a patient's neck and applying a magnetically-induced electrical impulse non-invasively to the target region within the neck to stimulate, inhibit or otherwise modulate selected nerve fibers that interact with the locus ceruleus. In another embodiment, surface electrodes are used to apply electrical impulses non-invasively to the target region within the neck to likewise stimulate, inhibit or otherwise modulate selected nerve fibers that interact with the locus ceruleus. Preferably, the target region is adjacent to, or in close proximity with, the carotid sheath that contains the vagus nerve.

The non-invasive magnetic stimulator device is used to modulate electrical activity of a vagus nerve, without actually introducing a magnetic field into the patient. The preferred stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described below, shaping an elongated electrical field of effect.

In another embodiment of the invention, the stimulator comprises a source of electrical power and two or more remote electrodes that are configured to stimulate a deep nerve. The stimulator comprises two electrodes that lie side-by-side within a hand-held enclosure, wherein the electrodes are separated by electrically insulating material. Each electrode is in continuous contact with an electrically conducting medium that extends from the interface element of the stimulator to the electrode. The interface element also contacts the patient's skin when the device is in operation.

Current passing through an electrode may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and an electrical field gradient of greater than 2 V/m/mm. Electric fields that are produced at the vagus nerve are generally sufficient to excite all myelinated A and B fibers, but not the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves that produce pain.

A cognitive fluctuation is a relatively abrupt change in the cognitive status of a dementia patient, which may be an hour-to-hour change or a day-to-day change. Treating or averting a cognitive fluctuation may be implemented within the context of control theory. A controller comprising, for example, one of the disclosed vagus nerve stimulators, a PID, and a feedforward model, provides input to the patient via stimulation of one or both of the patient's vagus nerves. Feedforward models may be black box models, particularly models that make use of support vector machines. Data for training and exercising the models are from noninvasive physiological and/or environmental signals obtained from sensors located on or about the patient. The model predicts the onset of a cognitive fluctuation, which may be avoided prophylactically through use of vagus nerve stimulation. If the cognitive fluctuation is in progress, the vagus nerve stimulation may terminate it.

The novel systems, devices and methods for treating dementia are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 shows that electrical stimulation of a vagus nerve in a normal (A) or Alzheimer (B) patient modulates the activity of resting state networks in the patient's brain, particularly the default mode network (DMN) and ventral attention network (VAN), through stimulation of the locus ceruleus via the nucleus tractus solitaris, such that norepinephrine is released into the networks.

FIG. 6 illustrates the approximate position of the housing of the stimulator according one embodiment of the present invention, when used to stimulate the right vagus nerve in the neck of a patient.

FIG. 7 illustrates the housing of the stimulator according one embodiment of the present invention, when positioned to stimulate a vagus nerve in the patient's neck, wherein the stimulator is applied to the surface of the neck in the vicinity of the identified anatomical structures.

DETAILED DESCRIPTION OF THE PREFERRED EMBODIMENTS

Figure 2A:
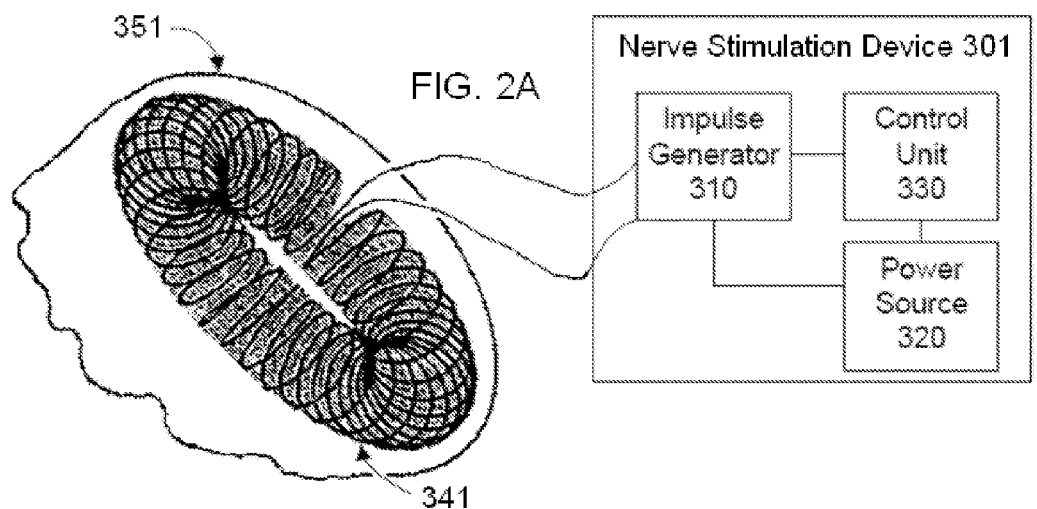
FIG. 2 shows a schematic view of nerve modulating devices according to the present invention, which supply controlled pulses of electrical current to (A) a magnetic stimulator coil or (B) to surface electrodes, and the figure also shows (C,D,E) an exemplary electrical voltage/current profile and waveform for stimulating, blocking and/or modulating impulses that are applied to a nerve.

In one embodiment, a time-varying magnetic field, originating and confined to the outside of a patient, generates an electromagnetic field and/or induces eddy currents within tissue of the patient. In another embodiment, electrodes applied to the skin of the patient generate currents within the tissue of the patient. An objective of the invention is to produce and apply electrical impulses that interact with the signals of one or more nerves to achieve the therapeutic result of altering the course of dementia, particularly Alzheimer's disease. Much of the disclosure will be directed specifically to treatment of a patient by electromagnetic stimulation in or around a vagus nerve, with devices positioned non-invasively on or near a patient's neck. In particular, the present invention can be used to indirectly stimulate or otherwise modulate nerves that innervate the locus ceruleus. However, it will be appreciated that the devices and methods of the present invention can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues.

Topics that are presented below in connection with the disclosure of the invention include the following: (1) Overview of physiological mechanisms by which vagus nerve stimulation may modulate norepinephrine levels by affecting the locus ceruleus, thereby altering the course of Alzheimer's disease; (2) Description of Applicant's magnetic and electrode-based nerve stimulating devices, describing in particular the electrical waveform used to stimulate a vagus nerve; (3) Preferred embodiments of the magnetic stimulator; (4) Preferred embodiments of the electrode-based stimulator; (5) Application of the stimulators to the neck of the patient; (6) Use of the devices with feedback and feedforward to improve treatment of individual patients.

Overview of Physiological Mechanisms Through which the Disclosed Vagus Nerve Stimulation Methods May be Used to Treat Patients with Dementia Alzheimer disease (AD) clinical decline and pathological processes occur gradually. AD is the end stage of many years of accumulation of pathological changes, which begin to develop decades before the earliest clinical symptoms occur. A pre-symptomatic phase occurs first, in which individuals are cognitively normal but some have AD pathological changes. This is followed by a second prodromal phase of AD, commonly referred to as mild cognitive impairment (MCI). The final phase of AD is dementia, defined as impairments that are severe enough to produce loss of function in learning and retaining newly acquired information (episodic declarative memory); in handling complex tasks and reasoning abilities (executive cognitive functions); in visuospatial ability and geographic orientation; and in language functions [David S. KNOPMAN. Alzheimer's Disease and other dementias. Chapter 409 (pp. 2274-2283) In: Goldman's Cecil Medicine, 24th Edn. (Lee Goldman and Andrew I. Schafer, Eds.). Philadelphia: Elsevier-Saunders, 2012; MASDEU J C, Kreisl W C, Berman K F. The neurobiology of Alzheimer disease defined by neuroimaging. Curr Opin Neurol 25(4, 2012):410-420; Charles DeCARLI. Mild cognitive impairment: prevalence, prognosis, aetiology, and treatment. Lancet Neurology 2 (2003): 15-21; Richard MAYEUX. Early Alzheimer's Disease. N Engl J Med 362 (2010): 2194-201; MUFSON E J, Binder L, Counts S E, DeKosky S T, de Toledo-Morrell L, Ginsberg S D, Ikonomovic M D, Perez S E, Scheff S W. Mild cognitive impairment: pathology and mechanisms. Acta Neuropathol 123(1, 2012):13-30].

Until recently, a definitive diagnosis of AD could only be made at autopsy or by brain biopsy of an individual, by identifying amyloid plaques and neurofibrillary tangles (NFTs) in the association regions of the individual's brain, particularly in the medial aspect of the temporal lobe. The amyloid plaques are comprised of amyloids, and the neurofibrillary tangles are comprised of tau protein. The development of amyloid plaques is necessary for the last of the hallmark AD-related lesions to develop, neuritic (senile) plaques, which are composed of a central core of beta-amyloid peptides aggregated together with fibrils of beta-amyloid, dystrophic neurites, reactive astrocytes, phagocytic cells, and other proteins and protein fragments derived from degenerating cells or liberated from neurons. Additional evidence of AD from an individual's autopsy or biopsy would include the presence of the following: the granulo-vacuolar degeneration of Shimkowicz, the neuropil threads of Braak, and neuronal loss with synaptic degeneration. In contrast, dementia with Lewy bodies is characterized at autopsy by the presence of Lewy bodies, which are lesions comprising clumps of alpha-synuclein and ubiquitin, rather than clumps of beta-amyloid.

Amyloid precursor protein (APP) is a membrane protein that is concentrated in the synapses of neurons. APP is the precursor molecule that, upon proteolysis, generates β-amyloid (Aβ), the peptide that forms amyloid fibrils, which in turn become the primary component of the amyloid plaques found in the brains of AD patients. The lipid transport protein apoE4 impairs Aβ clearance and promotes Aβ deposition, conferring an AD risk factor on individuals that carry apoE4.

Tau proteins, which are abundant in the central nervous system, stabilize microtubules. When tau proteins are defective and no longer stabilize microtubules properly, they can produce dementias, including AD. Defective tau protein will aggregate and twist into neurofibrillary tangles (NFTs), so that the protein is no longer available the stabilization of microtubules. As a result, the neuronal cytoskeleton falls apart, contributing to neuronal malfunction and cell death.

It is now thought that the earliest pathological evidence of Alzheimer's disease in humans (abnormally phosphorylated tau protein and pretangle material) appears most often in the locus ceruleus/subceruleus complex, which is a nucleus in the pons of the brainstem that is the principal site for brain synthesis of norepinephrine (noradrenaline). Such abnormal tau protein may appear in an individual before puberty or in early young adulthood [Heiko BRAAK and Kelly Del Tredici. The pathological process underlying Alzheimer's disease in individuals under thirty. Acta Neuropathol 121 (2011):171-181].

Despite the early involvement of the locus ceruleus in neurofibrillary tangle formation, a significant neuronal cell loss there may occur with a delay of 25 years, such that locus ceruleus cell loss in AD may be a relatively late but relatively rapid event [BUSCH C, Bohl J, Ohm T G. Spatial, temporal and numeric analysis of Alzheimer changes in the nucleus coeruleus. Neurobiol Aging 18(4, 1997):401-406; ZAROW C, Lyness S A, Mortimer J A, Chui H C. Neuronal loss is greater in the locus coeruleus than nucleus basalis and substantia nigra in Alzheimer and Parkinson diseases. Arch Neurol 6(3, 2003):337-341; GRUDZIEN A, Shaw P, Weintraub S, Bigio E, Mash D C, Mesulam M M. Locus coeruleus neurofibrillary degeneration in aging, mild cognitive impairment and early Alzheimer's disease. Neurobiol Aging 28(3, 2007):327-335; O'NEIL J N, Mouton P R, Tizabi Y, Ottinger M A, Lei D L, Ingram D K, Manaye K F. Catecholaminergic neuronal loss in locus coeruleus of aged female dtg APP/PS1 mice. J Chem Neuroanat 34(3-4, 2007): 102-107].

The mechanism of locus ceruleus cell loss is incompletely understood, but it appears to be a Wallerian-like degradation, in which damage to the neurons and/or microvessels that are innervated by locus ceruleus axons leads to death of the very same locus ceruleus cells that are innervating those damaged neurons and/or microvessels [HAGLUND M, Sjöbeck M, Englund E. Locus ceruleus degeneration is ubiquitous in Alzheimer's disease: possible implications for diagnosis and treatment. Neuropathology 26(6, 2006):528-32]. Thus, the site of initial damage to the locus ceruleus neuron appears to be its terminal field (e.g., near the senile plaque that it innervates), and perikaryal loss of the cell follows as a secondary retrograde change. Evidence in support of this mechanism is that there is a correlation between locus ceruleus degeneration and the density of plaques in regions of the cortex that are innervated by the locus ceruleus, and also that cortical-projecting neurons of the locus ceruleus degenerate selectively in AD [MARCYNIUK B, Mann D M, Yates P O. Loss of nerve cells from locus coeruleus in Alzheimer's disease is topographically arranged. Neurosci Lett 64(3, 1986):247-52; BONDAREFF W, Mountjoy C Q, Roth M. Loss of neurons of origin of the adrenergic projection to cerebral cortex (nucleus locus ceruleus) in senile dementia. Neurology 32(2, 1982):164-168; BONDAREFF W, Mountjoy C Q, Roth M, Rossor M N, Iversen L L, Reynolds G P, Hauser D L. Neuronal degeneration in locus ceruleus and cortical correlates of Alzheimer disease. Alzheimer Dis Assoc Disord 1(4, 1987):256-62; GERMAN D C, Manaye K F, White C L 3rd, Woodward D J, McIntire D D, Smith W K, Kalaria R N, Mann D M. Disease-specific patterns of locus coeruleus cell loss. Ann Neurol 32(5, 1992):667-76].

In AD rodent models, Aβ first deposits in the olfactory bulb of the brain, well before deposition in the brain structures that later develop rich Aβ deposits, with which impaired cognition is associated (the piriform cortex, entorhinal cortex, and hippocampus) [WESSON D W, Levy E, Nixon R A, Wilson D A Olfactory dysfunction correlates with beta-amyloid plaque burden in an Alzheimer's disease mouse model. J Neurosci 30 (2010):505-514; WESSON D W, Borkowski A H, Landreth G E, Nixon R A, Levy E, Wilson D A. Sensory network dysfunction, behavioral impairments, and their reversibility in an Alzheimer's β-amyloidosis mouse model. J Neurosci. 31(44, 2011): 15962-15971]. The invariable and severe involvement of the olfactory areas of the brain of human AD patients also raises the possibility that the olfactory pathway may be initially involved [PEARSON R C, Esiri M M, Hiorns R W, Wilcock G K, Powell T P. Anatomical correlates of the distribution of the pathological changes in the neocortex in Alzheimer disease. Proc Natl Acad Sci USA 82(13, 1985):4531-4534; FOSTER J, Sohrabi H, Verdile G, Martins R. Research criteria for the diagnosis of Alzheimer's disease: genetic risk factors, blood biomarkers and olfactory dysfunction. Int Psychogeriatr 20 (4, 2008):853-855; WILSON R S, Schneider J A, Arnold S E, Tang Y, Boyle P A, Bennett D A. Olfactory identification and incidence of mild cognitive impairment in older age. Arch Gen Psychiatry 64(7, 2007): 802-8; LI W, Howard J D, Gottfried J A. Disruption of odour quality coding in piriform cortex mediates olfactory deficits in Alzheimer's disease. Brain 133(9, 2010):2714-2726]. There is evidence that a noradrenergic deficiency induces the olfactory cognitive impairments through an alteration of olfactory neurogenesis [GUERIN D, Sacquet J, Mandairon N, Jourdan F, Didier A. Early locus coeruleus degeneration and olfactory dysfunctions in Tg2576 mice. Neurobiol Aging 30(2, 2009):272-83].

After the initial tau and amyloid-related pathologies, the pathology of AD patients' brains follows a course that allows for staging of the disease. The distribution of plaques may differ considerably from that of the neurofibrillary lesions, so staging of tau and amyloid-related pathologies are considered separately. Neurofibrillary tangles either antecede plaques or are formed independently. The tangles exhibit six stages of development. In Stage I, specific projection cells in the transentorhinal region are the first neurons to show the changes. It has been suggested that this corresponds to AD progressing from its initial site in the locus ceruleus to the transentorhinal region of the cerebral cortex, possibly via neuron-to-neuron transmission and transsynaptic transport of tau protein aggregates [Heiko BRAAK and Kelly Del Tredici. Alzheimer's pathogenesis: is there neuron-to-neuron propagation? Acta Neuropathol 121 (2011):589-595; REY N L, Jardanhazi-Kurutz D, Terwel D, Kummer M P, Jourdan F, Didier A, Heneka M T. Locus coeruleus degeneration exacerbates olfactory deficits in APP/PS1 transgenic mice. Neurobiol Aging. 33(2, 2012): 426.e1-426.e11]. Consequently, a brain region to which the earliest treatments of the present invention can be specifically directed is the transentorhinal region of the cerebral cortex, which would be appropriate for individuals in early adulthood or possibly even before puberty.

Stage II cases exhibit numerous transentorhinal NFTs and additional ones in the entorhinal region proper. Clinically, stage I and II cases are not associated with intellectual decline (preclinical phase). The pathologic process proceeds into both the hippocampal formation and the temporal neocortex (stage III), and then reaches further association areas of the basal neocortex (stage 1V). The neurofibrinary pathology then spreads superolaterally (stage V), eventually extending into the primary areas of the neocortex (stage VI). The late stages V-VI represent fully developed AD.

Amyloid-deposition occurs in three stages (A-C). The initial patches are seen in the basal neocortex, most frequently in poorly myelinated temporal areas such as the perirhinal and/or ectorhinal fields (stage A). Some individuals develop initial deposits in young adulthood. The depositions increase in number and spread into the adjoining neocortical areas and the hippocampal formation (stage B). Eventually, deposits are found in all areas of the cortex, including the densely myelinated primary areas of the neocortex (stage C) [BRAAK H, Braak E. Neuropathological staging of Alzheimer-related changes. Acta Neuropathologica 82 (1991): 239-259; BRAAK, H. and Braak, E. Staging of Alzheimer's disease-related neurofibrillary changes. Neurobiol. Aging 16 (1995): 271-278; Heiko BRAAK, Eva Braak, Jiirgen Bohl and Ralf Reintjes. Age, neurofibrillary changes, Abeta-amyloid and the onset of Alzheimer's disease. Neuroscience letters 210 (1996): 87-90; BRAAK, H. and Braak, E. Frequency of Stages of Alzheimer-Related Lesions in Different Age Categories. Neurobiology of Aging 18(4, 1997): 351-357; HYMAN B T, Gomez-Isla T. The natural history of Alzheimer neurofibrillary tangles and amyloid deposits. Neurobiol Aging 18(4, 1997):386-387; Bärbel SCHONHEIT, Rosemarie Zarski, Thomas G. Ohm. Spatial and temporal relationships between plaques and tangles in Alzheimer-pathology. Neurobiology of Aging 25 (2004): 697-711].

Symptoms of dementia are caused by dysfunction in portions of the brain that are responsible for memory, reasoning, spatial orientation, and language. The anatomical location of lesions in neurodegenerative diseases are not diffuse, random, or confluent, but are instead located in specific large-scale distributed networks. Thus, pathological changes in Alzheimer disease affect regions of the brain that are interconnected by well-defined groups of connections, and the disease process may extend along the interconnected nerve fibers. Maps of Aβ plaque locations can now be made noninvasively in living individuals using PET imaging [KLUNK, W. E., Engler, H., Nordberg, A., Wang, Y., Blomqvist, G., et al. Imaging brain amyloid in Alzheimer's disease with Pittsburgh Compound-B. Ann. Neurol., 55 (2004), 306-319]. Such images of Aβ plaques taken at the earliest stages of AD show a distribution that is remarkably similar to the anatomy of what is known as the default network [BUCKNER, R. L., Snyder, A. Z., Shannon, B. J., LaRossa, G., Sachs, R., et al. Molecular, structural, and functional characterization of Alzheimer's disease: evidence for a relationship between default activity, amyloid, and memory. J. Neurosci. 25 (2005):7709-7717; BUCKNER R L, Andrews-Hanna J R, Schacter D L. The brain's default network: anatomy, function, and relevance to disease. Ann NY Acad Sci 1124 (2008):1-38]. The default network includes the posterior cingulate, medial prefronta and bilateral inferior parietal cortices, and medial temporal lobe structures. Thus, specific brain regions that are active in the default network in young adults show amyloid deposition in older adults with AD. Consequently, a brain region to which treatments of the present invention can be specifically directed is the default network. The default network (and other so-called resting state networks) will be discussed below, after first summarizing what is known about the roles of Aβ plaques and Aβ oligomers in AD pathogenesis.

Until recently, it was generally agreed that AD begins when cells abnormally process the amyloid precursor protein (APP), which then leads to excess production or reduced clearance of β-amyloid (Aβ) in the patient's cortex. Excess of one or more forms of Aβ leads to a cascade, characterized by abnormal tau protein aggregation, synaptic dysfunction, cell death, and brain shrinkage. It is thought that extracellular deposits of Aβ in the brains of AD patients promote tau polymerization in the vicinity of the deposits, leading to the neuritic plaques. Additionally, a role in the pathogenesis of AD and other neurodegenerative diseases has been variously assigned to many factors that are known to be capable of damaging postmitotic cells, such as greater oxidative stress, mitochondrial dysfunction, chronic inflammation, and/or failure of the ubiquitin-proteasome system [John HARDY and Dennis J. Selkoe. The amyloid hypothesis of Alzheimer's disease: progress and problems on the road to therapeutics. Science 297 (2002): 353-356].

Despite the ability of the amyloid cascade hypothesis to organize much of what is known about the biochemistry and genetics of AD, the hypothesis provides an incomplete or unsatisfactory description of AD pathogenesis, for at least the following reasons. Plaques are found in cognitively normal individuals, and plaque burden does not correlate with memory decline. Removal of amyloid plaques by immunotherapy fails to improve cognition. Some forms of Aβ may actually be protective, rather than toxic. Injection of synthetic Aβ preparations fails to induce spreading of AD-related lesions. The amyloid cascade hypothesis also does not explain why certain populations of neurons are selectively vulnerable to neuronal death while others remain resistant. The absence of Aβ deposition in young individuals with abnormally phosphorylated tau protein (pretangle material) is not compatible with the amyloid cascade hypothesis, which assumes that Aβ drives AD pathogenesis and only secondarily induces intraneuronal tau changes [Christian HAASS. Initiation and propagation of neurodegeneration. Nature Medicine 16(11, 2010): 1201-1204; Heiko BRAAK and Kelly Del Tredici. The pathological process underlying Alzheimer's disease in individuals under thirty. Acta Neuropathol 121 (2011):171-181; CASTELLANI R J, Lee H G, Siedlak S L, Nunomura A, Hayashi T, Nakamura M, Zhu X, Perry G, Smith M A. Reexamining Alzheimer's disease: evidence for a protective role for amyloid-beta protein precursor and amyloid-beta. J Alzheimers Dis. 2009; 18(2):447-52; Siddhartha MONDRAGON-RODRIGUEZ, George Perry, Xiongwei Zhu, and Jannic Boehm. Amyloid beta and tau proteins as therapeutic targets for Alzheimer's disease treatment: rethinking the current strategy. Int J Alzheimers Dis. (2012); 2012: 630182, pp. 1-7].

Therefore, variants of the amyloid cascade hypothesis of AD pathogenesis have also been proposed. The revised models shift from the initial focus on amyloid plaques to the newer concept that AD memory failure is caused by small soluble oligomers of the Aβ peptide, toxins that target and disrupt particular synapses. According to this view, high concentrations of pathogenic Aβ and its oligomers reduce glutamatergic transmission, inhibit long-term potentiation and facilitate long-term depression, and they induce synapse loss and its associated cognitive impairment. Thus, theories of AD pathogenesis have shifted from Aβ plaques to the effects of Aβ oligomers on synapses [Rudolph E TANZI. The synaptic Aβ hypothesis of Alzheimer disease. Nature Neuroscience 8 (8, 2005): 977-979; Dennis J SELKOE. The ups and downs of Aβ. Nature Medicine 12(7, 2006): 758-759; FERREIRA S T, Klein W L. The Aβ oligomer hypothesis for synapse failure and memory loss in Alzheimer's disease. Neurobiol Learn Mem 96(4, 2011):529-43; KOFFIE R M, Hyman B T, Spires-Jones T L. Alzheimer's disease: synapses gone cold. Mol Neurodegener 6(1, 2011): 63, pp. 1-9; SHENG M, Sabatini B L, Salhof T C. Synapses and Alzheimer's disease. Cold Spring Harb Perspect Biol 4(5, 2012). pii: a005777, pp. 1-18].

Synaptically connected neurons form neural networks. Thus, an extension of synaptic dysfunction models of AD considers the effects of those synaptic dysfunctions on entire neural networks. At the network level, high concentrations of pathogenic Aβ and its oligomers cause dysrhythmias, including neuronal synchronization, epileptiform activity, seizures, and postictal suppression [DAMELIO M, Rossini P M. Brain excitability and connectivity of neuronal assemblies in Alzheimer's disease: From animal models to human findings. Prog Neurobiol 99(1, 2012):42-60; GEULA C. Abnormalities of neural circuitry in Alzheimer's disease: hippocampus and cortical cholinergic innervation. Neurology 51(1 Suppl 1, 1998):S18-29; GLEICHMANN M, Mattson M P. Alzheimer's disease and neuronal network activity. Neuromolecular Med 12(1, 2010):44-7; PALOP J J, Chin J, Mucke L. A network dysfunction perspective on neurodegenerative diseases. Nature 443(7113, 2006):768-773; PALOP J J, Mucke L. Synaptic depression and aberrant excitatory network activity in Alzheimer's disease: two faces of the same coin? Neuromolecular Med 12(1, 2010): 48-55; Jorge J. PALOP and Lennart Mucke. Amyloid-R Induced Neuronal Dysfunction in Alzheimer's Disease: From Synapses toward Neural Networks. Nat Neurosci 13(7, 2010): 812-818; SAVIOZ A, Leuba G, Vallet P G, Walzer C. Contribution of neural networks to Alzheimer disease's progression. Brain Res Bull 80(4-5, 2009):309-314; SEELEY W W, Crawford R K, Zhou J, Miller B L, Greicius M D. Neurodegenerative diseases target large-scale human brain networks. Neuron 62(1, 2009):42-52; SMALL D H. Network dysfunction in Alzheimer's disease: does synaptic scaling drive disease progression? Trends Mol Med 14(3, 2008):103-108; VERRET L, Mann E O, Hang G B, Barth A M, Cobos I, Ho K, Devidze N, Masliah E, Kreitzer A C, Mody I, Mucke L, Palop J J. Inhibitory interneuron deficit links altered network activity and cognitive dysfunction in Alzheimer model. Cell 149(3, 2012):708-721].

The manner in which AD may be spread between interconnected neurons within networks is not known, but several mechanisms have been suggested. First, early lesions within key synaptic convergence zones may disconnect or weaken functional circuits, thereby inducing deleterious network-wide compensations, leading to progressive degeneration within the circuit. Second, retrograde axonal transport deficits may cut off growth factor supply to long-range projection neurons, resulting in axonal degeneration, synapse loss, and post-synaptic dendrite retraction. Third, as seen in prion disease, misfolded disease proteins may themselves propagate along neural processes, then move throughout local and then long-range circuits via transsynaptic spread. Fourth, the network may exhibit some property, such as having an unusually high metabolic rate and/or being incessantly busy, that predisposes cells in the network to forming lesions or to the inability to repair lesions. These potential network degeneration mechanisms are not mutually exclusive.

Activation of a neural network is accompanied by oscillations within the network. Low frequency oscillations are likely associated with connectivity at the largest scale of the network, while higher frequencies are exhibited by smaller sub-networks within the larger network, which may be modulated by activity in the slower oscillating larger network. The default network, also called the default mode network (DMN), default state network, or task-negative network (TNN), is one such network that is characterized by coherent neuronal oscillations at a rate lower than 0.1 Hz. Other large scale networks also have this slow-wave property, but the default network is particularly relevant to the pathogenesis of AD because Aβ deposits form preferentially within it. Aβ deposits form within the DMN as individuals age, whether or not the individuals have dementia [BUCKNER, R. L., Snyder, A. Z., Shannon, B. J., LaRossa, G., Sachs, R., et al. Molecular, structural, and functional characterization of Alzheimer's disease: evidence for a relationship between default activity, amyloid, and memory. J. Neurosci. 25 (2005):7709-7717; BUCKNER R L, Andrews-Hanna J R, Schacter D L. The brain's default network: anatomy, function, and relevance to disease. Ann NY Acad Sci 1124 (2008):1-38; SPERLING R A, Laviolette P S, O'Keefe K, O'Brien J, Rentz D M, Pihlajamaki M, Marshall G, Hyman B T, Selkoe D J, Hedden T, Buckner R L, Becker J A, Johnson K A. Amyloid deposition is associated with impaired default network function in older persons without dementia. Neuron 63(2, 2009):178-188; DAMOISEAUX J S, Beckmann C F, Arigita E J, Barkhof F, Scheltens P, Stam C J, Smith S M, Rombouts S A. Reduced resting-state brain activity in the "default network" in normal aging. Cereb Cortex 18(8, 2008):1856-64; PALVA J M, Palva S. Infraslow fluctuations in electrophysiological recordings, blood-oxygenation-level-dependent signals, and psychophysical time series. Neuroimage 62(4, 2012):2201-2211; STEYN_ROSS M L, Steyn-Ross D A, Sleigh J W, Wilson M T. A mechanism for ultra-slow oscillations in the cortical default network. Bull Math Biol 73(2, 2011):398-416].

As the AD progresses, the DMN itself undergoes pathological changes internally and in terms of its connections to other slow-wave networks [GREICIUS M D, Srivastava G, Reiss A L, Menon V. Default-mode network activity distinguishes Alzheimer's disease from healthy aging: evidence from functional MRI. Proc Natl Acad Sci USA 101(13, 2004):4637-4642; MEVEL K, Chételat G, Eustache F, Desgranges B. The default mode network in healthy aging and Alzheimer's disease. Int J Alzheimers Dis. 2011; 2011: 535816. Epub 2011 Jun. 14, pp. 1-9; SORG C, Riedl V, Mühlau M, Calhoun V D, Eichele T, Läer L, Drzezga A, Förstl H, Kurz A, Zimmer C, Wohlschläger A M. Selective changes of resting-state networks in individuals at risk for Alzheimer's disease. Proc Natl Acad Sci USA 104(47, 2007):18760-18765; LI R, Wu X, Chen K, Fleisher A S, Reiman E M, Yao L. Alterations of Directional Connectivity among Resting-State Networks in Alzheimer Disease. AJNR Am J. Neuroradiol. 2012 Jul. 12. (Epub ahead of print, pp. 1-6); BRIER M R, Thomas J B, Snyder A Z, Benzinger T L, Zhang D, Raichle M E, Holtzman D M, Morris J C, Ances B M. Loss of intranetwork and internetwork resting state functional connections with Alzheimer's disease progression. J Neurosci 32(26, 2012):8890-9].

The default mode network corresponds to task-independent introspection (e.g., daydreaming), or self-referential thought. When the DMN is activated, the individual is ordinarily awake and alert, but the DMN may also be active during the early stages of sleep and during conscious sedation. The posterior cingulate cortex (PCC) and adjacent precuneus and the medial prefrontal cortex (mPFC) are the two most clearly delineated regions within the DMN. One reason that amyloid plaques form preferentially in the DMN may be that it is activated by default, when the brain is not otherwise engaged in specific tasks, and it is therefore on average more metabolically active than other such networks. Similarly, the DMN is vulnerable to developing Aβ deposition and Alzheimer disease pathology because, averaged over the course of a lifetime, it is the most synaptically active area of the brain, with the most cortical hubs. Thus, according to the synaptic Aβ hypothesis of Alzheimer disease, the Aβ deposits will form preferentially in the vicinity of those active synapses. A corollary of this line of reasoning is that education and other cognitive activity is protective against Alzheimer disease because it results in less activity, on average over a lifetime, within the DMN [RAICHLE M E, Snyder A Z. A default mode of brain function: a brief history of an evolving idea. Neuroimage 37(4, 2007):1083-1090; BROYD S J, Demanuele C, Debener S, Helps S K, James C J, Sonuga-Barke E J. Default-mode brain dysfunction in mental disorders: a systematic review. Neurosci Biobehav Rev 33(3, 2009):279-96; BUCKNER R L, Andrews-Hanna J R, Schacter D L. The brain's default network: anatomy, function, and relevance to disease. Ann NY Acad Sci 1124 (2008):1-38; BUCKNER R L, Sepulcre J, Talukdar T, Krienen F M, Liu H, Hedden T, Andrews-Hanna J R, Sperling R A, Johnson K A. Cortical hubs revealed by intrinsic functional connectivity: mapping, assessment of stability, and relation to Alzheimer's disease. J Neurosci 29 (2009):1860-1873; GREICIUS M D, Krasnow B, Reiss A L, Menon V. Functional connectivity in the resting brain: a network analysis of the default mode hypothesis. Proc Natl Acad Sci USA 100 (2003): 253-258].

During goal-oriented activity, the DMN is deactivated and one or more of several other networks, so-called task-positive networks (TPN), are activated. DMN activity is attenuated rather than extinguished during the transition between states, and is observed, albeit at lower levels, alongside task-specific activations. Strength of the DMN deactivation appears to be inversely related to the extent to which the task is demanding. Thus, DMN has been described as a task-negative network, given the apparent antagonism between its activation and task performance. Patients with AD appear to have problems deactivating their DMN [ROMBOUTS S A, Barkhof F, Goekoop R, Stam C J, Scheltens P. Altered resting state networks in mild cognitive impairment and mild Alzheimer's disease: an fMRI study. Hum Brain Mapp 26(4, 2005):231-239; WERMKE M, Sorg C, Wohlschläger A M, Drzezga A. A new integrative model of cerebral activation, deactivation and default mode function in Alzheimer's disease. Eur J Nucl Med Mol Imaging 35 (Suppl 1, 2008):512-524].

The term low frequency resting state networks (LFRSN or simply RSN) is used to describe both the task-positive and task-negative networks. Using independent component analysis (ICA) and related methods to assess coherence of fMRI Blood Oxygenation Level Dependent Imaging (BOLD) signals in terms of temporal and spatial variation, as well as variations between individuals, low frequency resting state networks in addition to the DMN have been identified, corresponding to different tasks. They are related to their underlying anatomical connectivity and replay at rest the patterns of functional activation evoked by the behavioral tasks. That is to say, brain regions that are commonly recruited during a task are anatomically connected and maintain in the resting state (in the absence of any stimulation) a significant degree of temporal coherence in their spontaneous activity, which is what allows them to be identified at rest [SMITH S M, Fox P T, Miller K L, Glahn D C, Fox P M, et al. Correspondence of the brain's functional architecture during activation and rest. Proc Natl Acad Sci USA 106 (2009): 13040-13045].

Frequently reported resting state networks (RSNs), in addition to the DMN, include the sensorimotor RSN, the executive control RSN, up to three visual RSNs, two lateralized fronto-parietal RSNs, the auditory RSN and the temporo-parietal RSN. However, different investigators use different methods to identify the low frequency resting state networks, so different numbers and somewhat different identities of RSNs are reported by different investigators [COLE D M, Smith S M, Beckmann C F. Advances and pitfalls in the analysis and interpretation of resting-state FMRI data. Front Syst Neurosci 4 (2010):8, pp. 1-15]. Examples of RSNs are described in publications cited by COLE and the following: ROSAZZA C, Minati L. Resting-state brain networks: literature review and clinical applications. Neurol Sci 32(5, 2011):773-85; ZHANG D, Raichle M E. Disease and the brain's dark energy. Nat Rev Neurol 6(1, 2010):15-28; DAMOISEAUX, J. S., Rombouts, S.A.R.B., Barkhof, F., Scheltens, P., Stam, C. J., Smith, S. M., Beckmann, C. F. Consistent resting-state networks across healthy subjects. Proc. Natl. Acad. Sci. U.S.A. 103 (2006): 13848-13853 FOX M D, Snyder A Z, Vincent J L, Corbetta M, Van Essen D C, Raichle M E. The human brain is intrinsically organized into dynamic, anticorrelated functional networks. Proc Natl Acad Sci USA 102 (2005):9673-9678].

For purposes of discussion, we adopt the set of resting state networks identified by LI et al, with the understanding that according to the above-cited publications, a more or less detailed set could also be adopted [LI R, Wu X, Chen K, Fleisher A S, Reiman E M, Yao L. Alterations of Directional Connectivity among Resting-State Networks in Alzheimer Disease. AJNR Am J. Neuroradiol. 2012 Jul. 12. [Epub ahead of print, pp. 1-6]. The resting state networks are shown in FIG. 1 for both normal individuals (FIG. 1A) and for individuals with advanced Alzheimer's disease (FIG. 1B). Also shown there are the connections between the networks, with the larger arrows indicating stronger connections. Solid and dashed arrows are, respectively, for positive and negative connections.

The resting state networks shown in FIG. 1 are as follows. The default-mode network (DMN) includes the posterior cingulate, medial prefronta and bilateral inferior parietal cortices, and the medial temporal lobe structures. The self-referential network (SRN) includes regions from the medial-ventral prefrontal cortex, the anterior cingulate, and the posterior cingulate. Previous investigators included the SRN in the DMN. As described above, the DMN is the principal site in which amyloid plaques and other pathologies related to AD occur.

The dorsal attention network (DAN) and ventral attention network (VAN) are two networks responsible for attentional processing. The VAN is involved in involuntary actions and exhibits increased activity upon detection of salient targets, especially when they appear in unexpected locations (bottom-up activity, e.g. when an automobile driver unexpectedly senses a hazard). The DAN is involved in voluntary (top-down) orienting and increases activity after presentation of cues indicating where, when, or to what individuals should direct their attention [FOX M D, Corbetta M, Snyder A Z, Vincent J L, Raichle M E. Spontaneous neuronal activity distinguishes human dorsal and ventral attention systems. Proc Natl Acad Sci USA 103 (2006):10046-10051; WEN X, Yao L, Liu Y, Ding M. Causal interactions in attention networks predict behavioral performance. J Neurosci 32(4, 2012):1284-1292]. The DAN is bilaterally centered in the intraparietal sulcus and the frontal eye field. The VAN is largely right lateralized in the temporal-parietal junction and the ventral frontal cortex.

The lateral visual network (LVN) and medial visual network (MVN) are two networks for visual processing and are respectively located in the lateral and medial parts of the visual cortex. The auditory network (AN) is responsible for auditory processing and is located in the bilateral superior temporal gyrus and in the primary and secondary auditory cortices. The sensory-motor network (SMN) is the network covering the somatosensory, premotor, and supplementary motor cortices. The LVN, MVN, AN, and SMN are four networks related to sensory processing, and the DMN, SRN, DAN, and VAN are associated with higher cognitive function.

The present invention modulates the activity of these resting state networks via the locus ceruleus by electrically stimulating the vagus nerve, as shown in FIG. 1. Stimulation of a network by that route may activate or deactivate a network, depending on the detailed configuration of adrenergic receptor subtypes within the network and their roles in enhancing or depressing neural activity within the network, as well as subsequent network-to-network interactions. According to the invention, preferential stimulation of a particular network, such as the DMN, may be accomplished by providing a vagus nerve stimulation signal that entrains to the signature EEG pattern of that network (see below and MANTINI D, Perrucci M G, Del Gratta C, Romani G L, Corbetta M. Electrophysiological signatures of resting state networks in the human brain. Proc Natl Acad Sci USA 104(32, 2007):13170-13175). By this method, it may be possible to preferentially attenuate or deactivate the DMN which, as described above, will decrease the progression of AD by reducing its metabolic activity and reduce the number of its synapses that are active in generating Aβ pathologies. Activation of another network such as the VAN may also produce the same effect, via network-to-network interactions. Another way that the stimulation resists AD pathogenesis is to increase the availability of norepinephrine in the DMN via the locus ceruleus which, as described below, counteracts the intense inflammation that occurs in the vicinity of Aβ-rich synapses. On a more global level, the reduced progression of AD by these mechanisms will also delay toxic effects in the terminal fields of locus ceruleus axons, thereby protecting the locus ceruleus from degradation and allowing it to continue counteracting the inflammation. Thus, although previous investigators have disclosed effects of vagus nerve stimulation on the hippocampus, which is altered in AD, the present invention goes far beyond that in disclosing the use of vagus nerve stimulation to affect whole resting state networks, including effects that one resting state network has on another resting state network. It also uses that stimulation in an effort to slow or stop progression of the AD, not simply treat cognitive symptoms of AD [SANCHEZ M M, Moghadam S, Naik P, Martin K J, Salehi A. Hippocampal network alterations in Alzheimer's disease and Down syndrome: from structure to therapy. J Alzheimers Dis. 2011; 26 Suppl 3:29-47; SHEN H, Fuchino Y, Miyamoto D, Nomura H, Matsuki N. Vagus nerve stimulation enhances perforant path-CA3 synaptic transmission via the activation of β-adrenergic receptors and the locus coeruleus. Int J Neuropsychopharmacol 15(4, 2012):523-30].

A vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves communicating the state of the viscera to the central nervous system.

The vagus (or vagal) afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 1). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra. Vagal afferents traverse the brainstem in the solitary tract, with some eighty percent of the terminating synapses being located in the nucleus of the tractus solitarius (or nucleus tractus solitarii, or NTS). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insular, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5, 1991):A3-A52].

With regard to vagal efferent nerve fibers, two vagal components have evolved in the brainstem to regulate peripheral parasympathetic functions. The dorsal vagal complex, consisting of the dorsal motor nucleus and its connections, controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus.

The locus ceruleus is also shown in FIG. 1. The vagus nerve transmits information to the locus ceruleus via the nucleus tractus solitarius (NTS), which has a direct projection to the dendritic region of the locus ceruleus. Other afferents to, and efferents from, the locus ceruleus are described by SARA et al, SAMUELS et al, and ASTON-JONES-SARA S J, Bouret S. Orienting and Reorienting: The Locus Coeruleus Mediates Cognition through Arousal. Neuron 76(1, 2012):130-41; SAMUELS E R, Szabadi E. Functional neuroanatomy of the noradrenergic locus coeruleus: its roles in the regulation of arousal and autonomic function part I: principles of functional organisation. Curr Neuropharmacol 6(3):235-53; SAMUELS, E. R., and Szabadi, E. Functional neuroanatomy of the noradrenergic locus coeruleus: its roles in the regulation of arousal and autonomic function part II: physiological and pharmacological manipulations and pathological alterations of locus coeruleus activity in humans. Curr. Neuropharmacol. 6 (2008), 254-285; Gary ASTON-JONES. Norepinephrine. Chapter 4 (pp. 47-57) in: Neuropsychopharmacology: The Fifth Generation of Progress (Kenneth L. Davis, Dennis Charney, Joseph T. Coyle, Charles Nemeroff, eds.) Philadelphia: Lippincott Williams & Wilkins, 2002].

In addition to the NTS, the locus ceruleus receives input from the nucleus gigantocellularis and its neighboring nucleus paragigantocellularis, the prepositus hypoglossal nucleus, the paraventricular nucleus of the hypothalamus, Barrington's nucleus, the central nucleus of the amygdala, and prefrontal areas of the cortex. These same nuclei may receive input from the NTS, such that stimulation of the vagus nerve may modulate the locus ceruleus via the NTS and then via a subsequent relay through these structures. In FIG. 1, these structures are labelled collectively as "Relay Nuclei."

The locus ceruleus has widespread projections throughout the cortex and is presumed to project to each of the resting state networks shown in FIG. 1, as indicated by arrows from the locus ceruleus to those networks [SAMUELS E R, Szabadi E. Functional neuroanatomy of the noradrenergic locus coeruleus: its roles in the regulation of arousal and autonomic function part I: principles of functional organisation. Curr Neuropharmacol 6 (3):235-53]. It also projects to subcortical regions, notably the raphe nuclei, which release serotonin to the rest of the brain, including the resting state networks shown in FIG. 1. An increased dorsal raphe nucleus firing rate is thought to be secondary to an initial increased locus ceruleus firing rate from vagus nerve stimulation [Adrienne E. DORR and Guy Debonnelv. Effect of vagus nerve stimulation on serotonergic and noradrenergic transmission. J Pharmacol Exp Ther 318(2, 2006):890-898; MANTA S, Dong J, Debonnel G, Blier P. Enhancement of the function of rat serotonin and norepinephrine neurons by sustained vagus nerve stimulation. J Psychiatry Neurosci 34(4, 2009):272-80]. In AD, extensive serotonergic denervation occurs, and reduced serotonin in the cortex is likely due to loss of projections from the raphe nuclei. As with the locus ceruleus, the raphe nuclei are a site of neurofibrillatory tangles and neuron loss. Consequently, stimulation of the raphe nuclei, either via the nucleus tractus solitarius or via the locus ceruleus may inhibit degradation of the raphe nuclei. Protection of the locus ceruleus would accordingly also protect the raphe nuclei. This may be of significance particularly as it relates to the neuropsychiatric aspects of AD [FRANCIS P T, Ramírez M J, Lai M K. Neurochemical basis for symptomatic treatment of Alzheimer's disease. Neuropharmacology 59(4-5, 2010):221-229].

The locus ceruleus also has projections to autonomic nuclei, including the dorsal motor nucleus of the vagus, as shown in FIG. 1 [FUKUDA, A., Minami, T., Nabekura, J., Oomura, Y. The effects of noradrenaline on neurones in the rat dorsal motor nucleus of the vagus, in vitro. J. Physiol., 393 (1987): 213-231; MARTINEZ-PENA y Valenzuela, I., Rogers, R. C., Hermann, G. E., Travagli, R. A. (2004) Norepinephrine effects on identified neurons of the rat dorsal motor nucleus of the vagus. Am. J. Physiol. Gas-trointest. Liver Physiol., 286, G333-G339; TERHORST, G. J., Toes, G. J., Van Willigen, J. D. Locus coeruleus projections to the dorsal motor vagus nucleus in the rat. Neuroscience, 45 (1991): 153-160].

Although the locus ceruleus is presumed to project to all of the resting networks shown in FIG. 1, it is thought to project most strongly to the ventral attention network (VAN), which is indicated by a thicker arrow than the arrows to the other networks [CORBETTA M, Patel G, Shulman G L. The reorienting system of the human brain: from environment to theory of mind. Neuron 58(3, 2008):306-24; MANTINI D, Corbetta M, Perrucci M G, Romani G L, Del Gratta C. Large-scale brain networks account for sustained and transient activity during target detection. Neuroimage 44(1, 2009):265-274]. The attention systems (VAN and DAN) have been investigated long before their identification as resting state networks, and functions attributed to the VAN have in the past been attributed to the locus ceruleus/noradrenaline system [ASTON-JONES G, Cohen J D. An integrative theory of locus coeruleus-norepinephrine function: adaptive gain and optimal performance. Annu Rev Neurosci 28 (2005):403-50; BOURET S, Sara S J. Network reset: a simplified overarching theory of locus coeruleus noradrenaline function. Trends Neurosci 28(11, 2005):574-82; SARA S J, Bouret S. Orienting and Reorienting: The Locus Coeruleus Mediates Cognition through Arousal. Neuron 76(1, 2012):130-41; PETERSEN S E, Posner M I. The attention system of the human brain: 20 years after. Annu Rev Neurosci 35 (2012):73-89; BERRIDGE C W, Waterhouse B D. The locus coeruleus-noradrenergic system: modulation of behavioral state and state-dependent cognitive processes. Brain Res Brain Res Rev 42(1, 2003):33-84].

Locus ceruleus neurons exhibit both tonic and phasic activity modes. Tonic activity is low in an unaroused state that facilitates sleep and disengagement from the environment, moderate when the individual is engaged in a focused task of high utility and filtering out irrelevant stimuli, and high when the organism is not committed to a task but is responsive to unanticipated changes in the environment. Individuals with low tonic activity are not alert, and individuals with high tonic activity are easily distracted and anxious. The second component of locus ceruleus discharge is the phasic response to stimuli. The phasic signal may be understood to be an "interrupt" signal that allows the flexible configuration of a target network once a target is detected, which is to say, a reorienting from one task state to another. When utility of the phasic activity relative to in the task wanes, locus ceruleus neurons revert to a tonic activity mode, which would often correspond to either the low-tone unaroused state or the high-tone distractable state.

Many processes in addition to those that produce of Aβ oligomers at synapses contribute to the pathology of AD [QUERFURTH H W, LaFerla F M. Alzheimer's disease. N Engl J Med 362(4, 2010):329-44; ZLOKOVIC B V. Neurovascular pathways to neurodegeneration in Alzheimer's disease and other disorders. Nat Rev Neurosci 12(12, 2011): 723-38]. Prominent among the additional processes is the intense inflammation that occurs in the vicinity of such synapses [WYSS-CORAY T, Rogers J. Inflammation in Alzheimer disease—a brief review of the basic science and clinical literature. Cold Spring Harb Perspect Med 2(1, 2012):a006346, pp. 1-23; Jose Miguel RUBIO-PEREZ and Juana Maria Morillas-Ruiz. A Review: Inflammatory Process in Alzheimer's Disease, Role of Cytokines. The Scientific World Journal Volume 2012, Article ID 756357, pp. 1-15]. Activated microglia and reactive astrocytes localize to fibrillar plaques, and the phagocytic microglia engulf and degrade Aβ. However, chronically activated microglia release chemokines and a cascade of damaging cytokines. Astrocytes also respond quickly with changes in their morphology, antigenicity, and function, and, like microglia, these reactive states have initial beneficial but subsequent destructive consequences. Overexpression of interleukin (IL)-1 is one such destructive consequence, which produces many reactions in a vicious circle that cause dysfunction and neuronal death.

There is considerable evidence that the release of norepinephrine by the locus ceruleus to the sites of the inflammation acts to reduce the inflammation. In so doing, the locus ceruleus protects itself from damage to the terminal fields of its axons, thereby limiting subsequent death of its own cells by what was described above as a Wallerian-like degradation [COUNTS S E, Mufson E J. Noradrenaline activation of neurotrophic pathways protects against neuronal amyloid toxicity. J Neurochem 113(3, 2010):649-60; WENK G L, McGann K, Hauss-Wegrzyniak B, Rosi S. The toxicity of tumor necrosis factor-alpha upon cholinergic neurons within the nucleus basalis and the role of norepinephrine in the regulation of inflammation: implications for Alzheimer's disease. Neuroscience 121(3, 2003):719-29; KALININ S, Gavrilyuk V, Polak P E, Vasser R, Zhao J, Heneka M T, Feinstein D L. Noradrenaline deficiency in brain increases beta-amyloid plaque burden in an animal model of Alzheimer's disease. Neurobiol Aging 28(8, 2007):1206-1214; HENEKA M T, Ramanathan M, Jacobs A H, Dumitrescu-Ozimek L, Bilkei-Gorzo A, Debeir T, Sastre M, Galldiks N, Zimmer A, Hoehn M, Heiss W D, Klockgether T, Staufenbiel M. Locus ceruleus degeneration promotes Alzheimer pathogenesis in amyloid precursor protein 23 transgenic mice. J. Neurosci. 26(5, 2006):1343-54; HENEKA M T, Nadrigny F, Regen T, Martinez-Hernandez A, Dumitrescu-Ozimek L, Terwel D, Jardanhazi-Kurutz D, Walter J, Kirchhoff F, Hanisch U K, Kummer M P. Locus ceruleus controls Alzheimer's disease pathology by modulating microglial functions through norepinephrine. Proc Natl Acad Sci USA. 107(13, 2010):6058-6063; JARDANHAZI-KURUTZ D, Kummer M P, Terwel D, Vogel K, Thiele A, Heneka M T. Distinct adrenergic system changes and neuroinflammation in response to induced locus ceruleus degeneration in APP/PS1 transgenic mice. Neuroscience 176 (2011):396-407; YANG J H, Lee E O, Kim S E, Suh Y H, Chong Y H. Norepinephrine differentially modulates the innate inflammatory response provoked by amyloid-R peptide via action at β-adrenoceptors and activation of cAMP/PKA pathway in human THP-1 macrophages. Exp Neurol 236(2, 2012):199-206; KONG Y, Ruan L, Qian L, Liu X, Le Y. Norepinephrine promotes microglia to uptake and degrade amyloid beta peptide through upregulation of mouse formyl peptide receptor 2 and induction of insulin-degrading enzyme. J Neurosci 30(35, 2012):11848-11857; KALININ S, Polak P E, Lin S X, Sakharkar A J, Pandey S C, Feinstein D L. The noradrenaline precursor L-DOPS reduces pathology in a mouse model of Alzheimer's disease. Neurobiol Aging 33(8, 2012):1651-1663; HAMMERSCHMIDT T, Kummer M P, Terwel D, Martinez A, Gorji A, Pape H C, Rommelfanger K S, Schroeder J P, Stoll M, Schultze J, Weinshenker D, Heneka M T. Selective Loss of Noradrenaline Exacerbates Early Cognitive Dysfunction and Synaptic Deficits in APP/PS1 Mice. Biol Psychiatry. 2012 Aug. 9. Epub ahead of print, pp. 1-10; O'DONNELL J, Zeppenfeld D, McConnell E, Pena S, Nedergaard M. Norepinephrine: A Neuromodulator That Boosts the Function of Multiple Cell Types to Optimize CNS Performance. Neurochem Res. 2012 Jun. 21. (Epub ahead of print}, pp. 1-17].

Because stimulation of the vagus nerve can preferentially enhance norepinephrine levels at selected central nervous system sites through the judicious choice of electrical stimulation parameters, its use is potentially superior to the indiscriminant enhancement of norepinephrine levels by pharmacological methods, because potential side effects would be minimized by the former electrical stimulation method. Efficacy of the vagus nerve stimulation in this regard may be monitored and evaluated, for example, by imaging neuroinflammation in the brain [MASDEU J C, Kreisl W C, Berman K F. The neurobiology of Alzheimer disease defined by neuroimaging. Curr Opin Neurol 25(4, 2012):410-420; JACOBS A H, Tavitian B; INMiND consortium. Noninvasive molecular imaging of neuroinflammation. J Cereb Blood Flow Metab 32(7, 2012):1393-1415; CHAUVEAU F, Boutin H, Van Camp N, Done F, Tavitian B. Nuclear imaging of neuroinflammation: a comprehensive review of [11C]PK11195 challengers. Eur J Nucl Med Mol Imaging 35(12, 2008):2304-19].

Although the present invention is directed primarily to slowing or stopping the progression of the long-term course of AD, it is also understood that the invention may have a shorter-term beneficial effect on the cognitive state of AD patients, particularly those who experience cognitive fluctuations [ROBERTSON I H. A noradrenergic theory of cognitive reserve: implications for Alzheimer's disease. Neurobiol Aging. 2012 Jun. 26. (Epub ahead of print), pp. 1-11]. The role of resting state networks in attentional fluctuations has heretofore been discussed almost entirely in terms of attention deficit hyperactivity disorder (ADHD) and related disorders [SONUGA-BARKE E J, Castellanos F X. Spontaneous attentional fluctuations in impaired states and pathological conditions: a neurobiological hypothesis. Neurosci Biobehav Rev. 2007; 31(7, 2007):977-86]. However, JU et al compared resting state networks in subjects with mild or uncertain Alzheimer's disease with cognitive fluctuations, to those without cognitive fluctuations, as well as to healthy controls, to assess whether cognitive fluctuations are associated with abnormalities in resting state networks. The subjects with fluctuations had decreased daytime alertness and increased frequency of other sleep symptoms. The investigators found that there was decreased connectivity in both default mode and dorsal attention networks in the group with fluctuations (DMN and DAN, respectively in FIG. 1, with the self-referential network SRN being ordinarily being considered part of DMN). Furthermore, there was decreased anti-correlation between the two networks tested. Other resting state networks were not investigated, and correction for changes due to normal aging were not performed [Yo-El S. JU, Linda Larson-Prior, and James Galvin. Cognitive Fluctuations are Associated with Abnormalities in Resting-State Functional Networks. SLEEP 2010 (the 24th Annual Meeting of the Associated Professional Sleep Societies, Jun. 6-9, 2010, San Antonio, Tex.): Poster 70, Abstract 0109].

JU et al also proposed that individuals with cognitive fluctuations constitute a subset of individuals with mild cognitive impairment or AD, whose course of degeneration may be distinct from typical AD, so that the connections shown in FIG. 1 would not necessarily apply to cognitive fluctuators. According to FIG. 1, in a normal individual, SRN/DMN would activate VAN which then activates DAN, and that activation would deactivate DMN, possibly with the aid of VAN, so that the individual can concentrate on the task at hand without the distraction produced by an active DMN. In the Alzheimer patient, the connections are altered, and the networks themselves are altered. But according to FIG. 1, the alterations are likely to involve a decreased connectivity to VAN, such that VAN would not be able to perform its normal role in promoting concentration on the part of the cognitive fluctuator. According to the present invention, stimulation of VAN by vagus nerve stimulation would compensate for that altered VAN connectivity by providing extra norepinephrine to VAN, thereby resetting the networks of the patient from one temporarily trapped in an innatentive global state to one in which more normal concentration is possible.

Description of the Magnetic and Electrode-Based Nerve Stimulating/Modulating Devices Methods and devices of the invention that are used to stimulate a vagus nerve will now be described. Either a magnetic stimulation device or an electrode-based device may be used for that purpose. FIG. 2A is a schematic diagram of Applicant's magnetic nerve stimulating/modulating device 301 for delivering impulses of energy to nerves for the treatment of medical conditions such as dementia. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 2A to be a single coil, in practice the coil may also comprise two or more distinct coils, each of which is connected in series or in parallel to the impulse generator 310. Thus, the coil 341 that is shown in FIG. 2A represents all the magnetic stimulator coils of the device collectively. In a preferred embodiment that is discussed below, coil 341 actually contains two coils that may be connected either in series or in parallel to the impulse generator 310.

The item labeled in FIG. 2A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below, the conducting medium with which the coil 341 is in contact need not completely surround the toroid.

The design of the magnetic stimulator 301, which is also adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

Figure 2B:
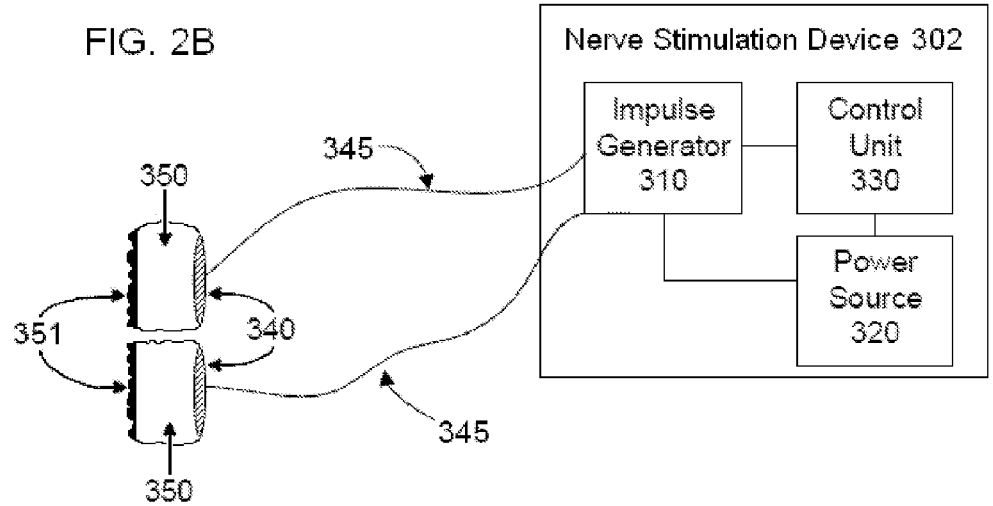

An alternate embodiment of the present invention is shown in FIG. 2B, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 2B, in practice the electrodes may also comprise three or more distinct electrode elements, each of which is connected in series or in parallel to the impulse generator 310. Thus, the electrodes 340 that are shown in FIG. 2B represent all electrodes of the device collectively.

The item labeled in FIG. 2B as 350 is a volume, contiguous with an electrode 340, that is filled with electrically conducting medium. As described below in connection with particular embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 8), analog-to-digital converters for digitizing externally supplied analog signals (see FIG. 8), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmur ǂo, Przemys ǂaw P ǂonecki, Jacek Starzyński, Stanis ǂ law Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 2C:
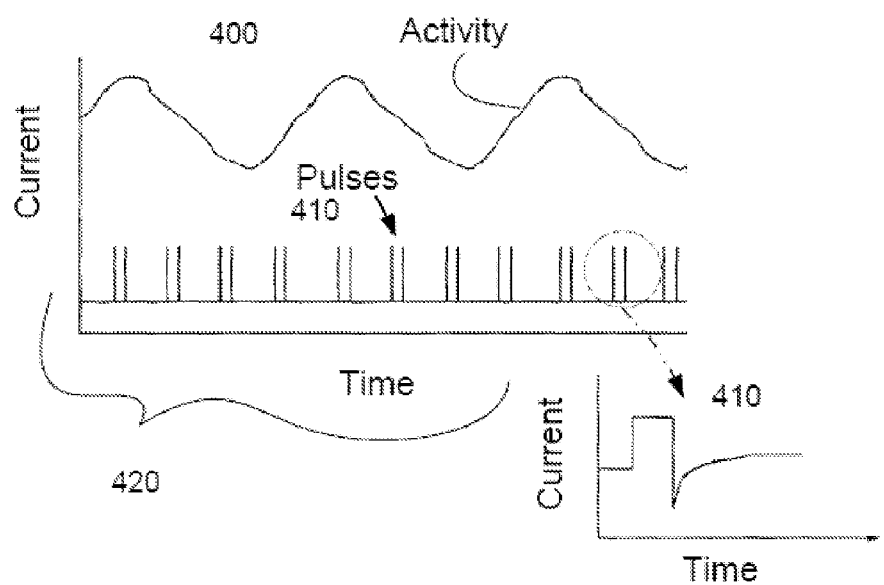

FIG. 2C illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 100 Hz, more preferably around 25 Hz. The modulation signal may have a pulse width selected to influence the therapeutic result, such as about 1 microseconds to about 1000 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J. Struijk. A comparative study of three techniques for diameter selective fiber activation in the vagal nerve: anodal block, depolarizing prepulses and slowly rising pulses. J. Neural Eng. 5(2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2D:
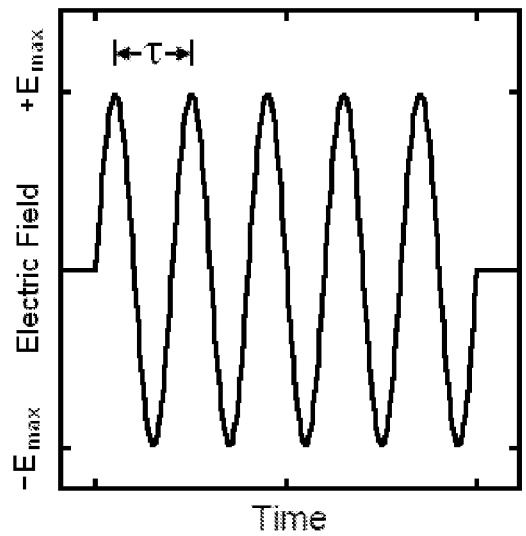
Figure 2E:
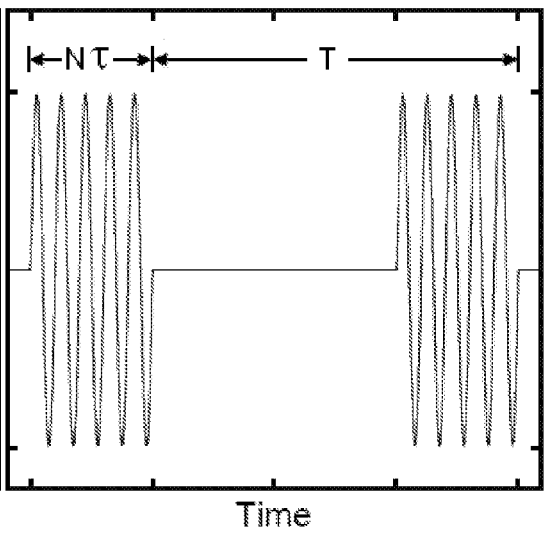

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2D and 2E. As seen there, individual sinusoidal pulses have a period of, and a burst consists of N such pulses. This is followed by a period with no signal (the inter-burst period). The pattern of a burst followed by silent inter-burst period repeats itself with a period of T. For example, the sinusoidal period may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2E to make the bursts discernable). When these exemplary values are used for T and, the waveform contains significant Fourier components at higher frequencies ($\frac{1}{200}$ microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10 (1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2D and 2E may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011].

Those methods involve high-frequency modulation in the range of from about 1.5 KHz to about 50 KHz, which is applied to the patient's spinal cord region. However, such methods are different from the present invention because, for example, they is invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2 (2000):477-509].

Figure 8:
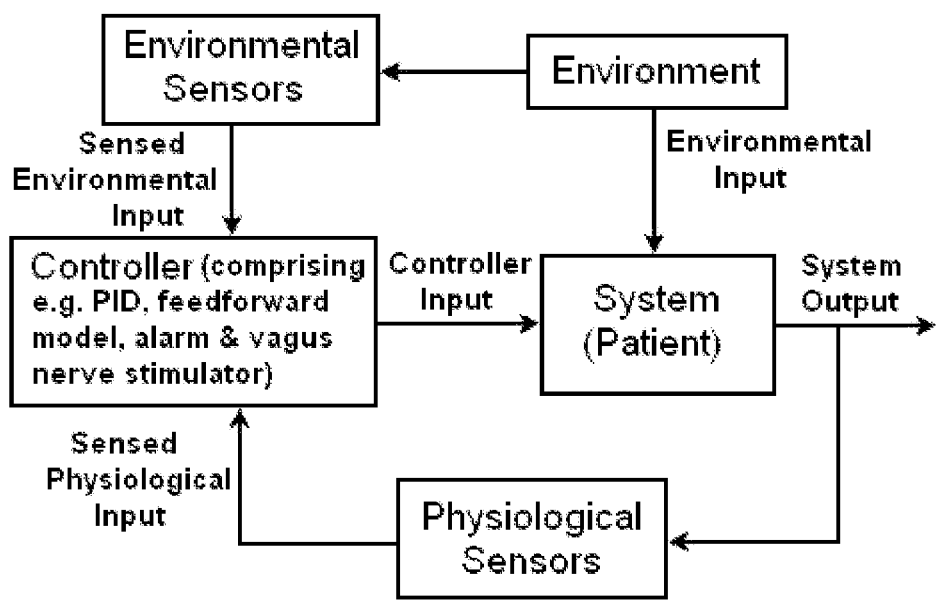
FIG. 8 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 8). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

Preferred Embodiments of the Magnetic Stimulator

A preferred embodiment of magnetic stimulator coil 341 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, (UMI Microform Number: 9940153, UMI Company, Ann Arbor Mich.)].

Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e, z and are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein.

Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions. The shaping of the electric field is described in terms of the corresponding field equations in commonly assigned application US20110125203 (application Ser. No. 12/964,050), entitled Magnetic stimulation devices and methods of therapy, to SIMON et al., which is hereby incorporated by reference.

Thus, the present invention differs from the device disclosed by CARBUNARU and Durand by deliberately shaping an electric field that is used to transcutaneously stimulate the patient. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima. In the dissertation cited above, Carbunaru-FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity of the conducting material and select boundary conditions, thereby shaping the electric fields and currents as described above, but also to create devices that can be applied practically to any surface of the body. The volume of the container containing electrically conducting medium is labeled in FIG. 2A as 351. Use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. This allows for minimal heating of the coil(s) and deeper tissue stimulation. However, application of the conducting medium to the surface of the patient is difficult to perform in practice because the tissue contours (head, arms, legs, neck, etc.) are not planar. To solve this problem, in the preferred embodiment of the present invention, the toroidal coil is embedded in a structure which is filled with a conducting medium having approximately the same conductivity as muscle tissue, as now described.

In one embodiment of the invention, the container contains holes so that the conducting material (e.g., a conducting gel) can make physical contact with the patient's skin through the holes. For example, the conducting medium 351 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J. Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 341 in FIG. 2A reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain other peripheral nerves.

This preferred embodiment of the magnetic stimulation device is shown in FIG. 3. FIGS. 3A and 3B respectively provide top and bottom views of the outer surface of the toroidal magnetic stimulator 30. FIGS. 3C and 3D respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
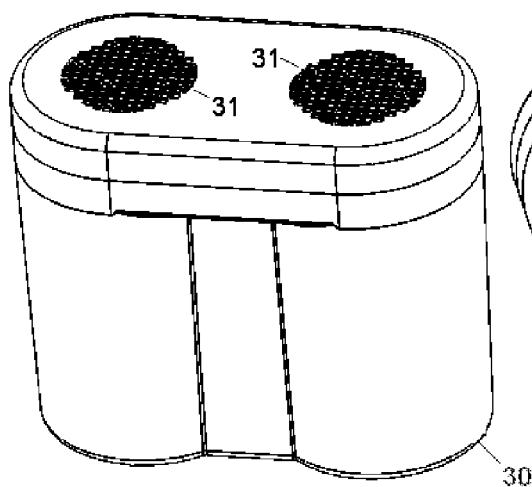
FIG. 3 illustrates a dual-toroid magnetic stimulator coil according to an embodiment of the present invention, which is shown to be situated within a housing that contains electrically conducting material (A-D), and it also shows the housing and cap of the dual-toroid magnetic stimulator attached via cable to a box containing the device's impulse generator, control unit, and power source (E).
Figure 3B:
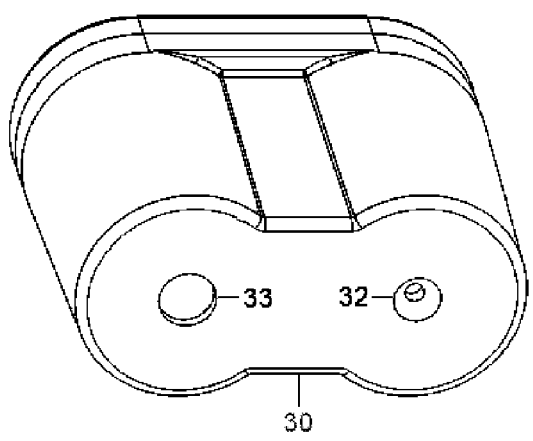
Figure 3C:
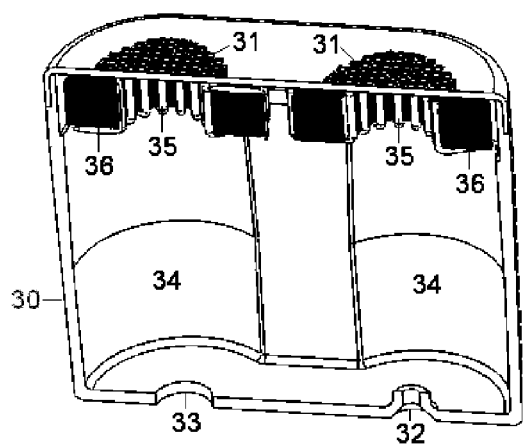
Figure 3D:
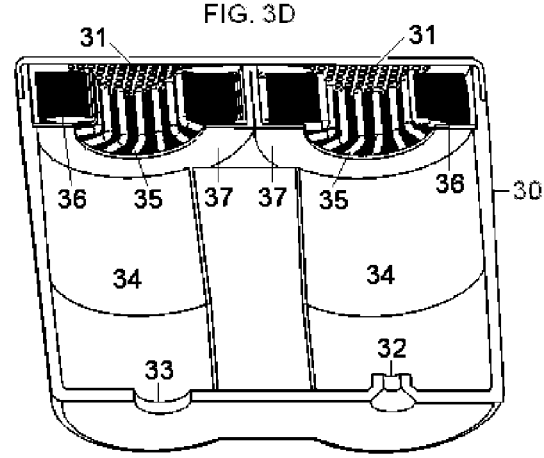

FIGS. 3B-3D show openings at the opposite end of the stimulator 30. One of the openings is an electronics port 32 through which wires pass from the stimulator coil(s) to the impulse generator (310 in FIG. 2A). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (4, 2001): 434-441].

FIGS. 3C and 3D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

Signal generators for magnetic stimulators have been described for commercial systems [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006], as well as for custom designs for a control unit 330, impulse generator 310 and power source 320 [Eric BASHAM, Zhi Yang, Natalia Tchemodanov, and Wentai Liu. Magnetic Stimulation of Neural Tissue: Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to Charles M. Epstein; U.S. Pat. No. 5,718,662, entitled Apparatus for the magnetic stimulation of cells or tissue, to Reza Jalinous; U.S. Pat. No. 5,766,124, entitled Magnetic stimulator for neuro-muscular tissue, to Poison]. Conventional magnetic nerve stimulators use a high current impulse generator that may produce discharge currents of 5,000 amps or more, which is passed through the stimulator coil, and which thereby produces a magnetic pulse. Typically, a transformer charges a capacitor in the impulse generator 310, which also contains circuit elements that limit the effect of undesirable electrical transients. Charging of the capacitor is under the control of a control unit 330, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus.

Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology 85 (1992): 253-264; Nafia A L-MUTAWALY, Hubert de Bruin, and Gary Hasey. The effects of pulse configuration on magnetic stimulation. Journal of Clinical Neurophysiology 20(5):361-370, 2003].

Furthermore, a potential practical disadvantage of using magnetic stimulator coils is that they may overheat when used over an extended period of time. Use of the above-mentioned toroidal coil and container of electrically conducting medium addresses this potential disadvantage. However, because of the poor coupling between the stimulating coils and the nerve tissue, large currents are nevertheless required to reach threshold electric fields. At high repetition rates, these currents can heat the coils to unacceptable levels in seconds to minutes depending on the power levels and pulse durations and rates. Two approaches to overcome heating are to cool the coils with flowing water or air or to increase the magnetic fields using ferrite cores (thus allowing smaller currents). For some applications where relatively long treatment times at high stimulation frequencies may be required, neither of these two approaches are adequate. Water-cooled coils overheat in a few minutes. Ferrite core coils heat more slowly due to the lower currents and heat capacity of the ferrite core, but also cool off more slowly and do not allow for water-cooling since the ferrite core takes up the volume where the cooling water would flow.

A solution to this problem is to use a fluid which contains ferromagnetic particles in suspension like a ferrofluid, or magnetorheological fluid as the cooling material. Ferrofluids are colloidal mixtures composed of nanoscale ferromagnetic, or ferrimagnetic, particles suspended in a carrier fluid, usually an organic solvent or water. The ferromagnetic nanoparticles are coated with a surfactant to prevent their agglomeration (due to van der Waals forces and magnetic forces). Ferrofluids have a higher heat capacity than water and will thus act as better coolants. In addition, the fluid will act as a ferrite core to increase the magnetic field strength. Also, since ferrofluids are paramagnetic, they obey Curie's law, and thus become less magnetic at higher temperatures. The strong magnetic field created by the magnetic stimulator coil will attract cold ferrofluid more than hot ferrofluid thus forcing the heated ferrofluid away from the coil. Thus, cooling may not require pumping of the ferrofluid through the coil, but only a simple convective system for cooling. This is an efficient cooling method which may require no additional energy input [U.S. Pat. No. 7,396,326 and published applications US2008/0114199, US2008/0177128, and US2008/0224808, all entitled Ferrofluid cooling and acoustical noise reduction in magnetic stimulators, respectively to Ghiron et al., Riehl et al., Riehl et al. and Ghiron et al.].

Magnetorheological fluids are similar to ferrofluids but contain larger magnetic particles which have multiple magnetic domains rather than the single domains of ferrofluids. [U.S. Pat. No. 6,743,371, Magneto sensitive fluid composition and a process for preparation thereof, to John et al.]. They can have a significantly higher magnetic permeability than ferrofluids and a higher volume fraction of iron to carrier. Combinations of magnetorheological and ferrofluids may also be used [M T LOPEZ-LOPEZ, P Kuzhir, S Lacis, G Bossis, F Gonzalez-Caballero and J D G Duran. Magnetorheology for suspensions of solid particles dispersed in ferrofluids. J. Phys.: Condens. Matter 18 (2006) S2803-S2813; Ladislau VEKAS. Ferrofluids and Magnetorheological Fluids. Advances in Science and Technology Vol. 54 (2008) pp 127-136.].

Commercially available magnetic stimulators include circular, parabolic, figure-of-eight (butterfly), and custom designs that are available commercially [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006]. Additional embodiments of the magnetic stimulator coil 341 have been described [U.S. Pat. No. 6,179,770, entitled Coil assemblies for magnetic stimulators, to Stephen Mould; Kent DAVEY. Magnetic Stimulation Coil and Circuit Design. IEEE Transactions on Biomedical Engineering, Vol. 47 (No. 11, November 2000): 1493-1499]. Many of the problems that are associated with such conventional magnetic stimulators, e.g., the complexity of the impulse-generator circuitry and the problem with overheating, are largely avoided by the toroidal design shown in FIG. 3.

Figure 3E:
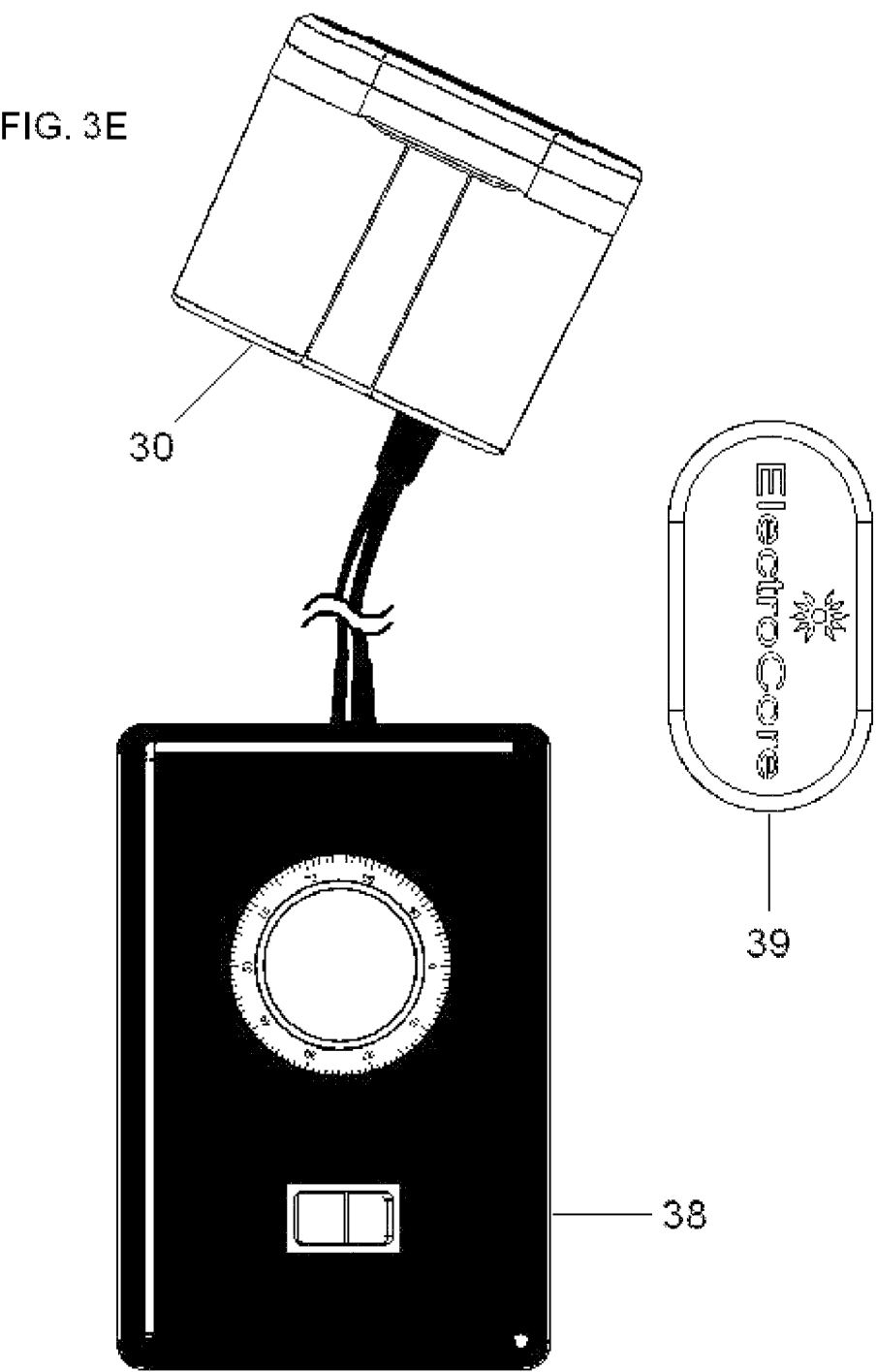

Thus, use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. Therefore, with the present invention, it is possible to generate waveforms shown in FIG. 2 with relatively simple, low-power circuits that are powered by batteries. The circuits may be enclosed within a box 38 as shown in FIG. 3E, or the circuits may be attached to the stimulator itself (FIG. 3A-3D) to be used as a hand-held device. In either case, control over the unit may be made using only an on/off switch and power knob. The only other component that may be needed might be a cover 39 to keep the conducting fluid from leaking or drying out between uses. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIGS. 2D and 2E, shaping an elongated electrical field of effect.

Preferred Embodiments of the Electrode-Based Stimulator

In another embodiment of the invention, electrodes applied to the surface of the neck, or to some other surface of the body, are used to non-invasively deliver electrical energy to a nerve, instead of delivering the energy to the nerve via a magnetic coil. The vagus nerve has been stimulated previously non-invasively using electrodes applied via leads to the surface of the skin. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of dementia. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of dementia.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. However, none of the disclosures in these patents or patent applications for electrical stimulation of the vagus nerve at the ear are used to treat dementia.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

Considering that the nerve stimulating device 301 in FIG. 2A and the nerve stimulating device 302 in FIG. 2B both control the shape of electrical impulses, their functions are analogous, except that one stimulates nerves via a pulse of a magnetic field, and the other stimulates nerves via an electrical pulse applied through surface electrodes. Accordingly, general features recited for the nerve stimulating device 301 apply as well to the latter stimulating device 302 and will not be repeated here. The preferred parameters for each nerve stimulating device are those that produce the desired therapeutic effects.

A preferred embodiment of an electrode-based stimulator is shown in FIG. 4A. A cross-sectional view of the stimulator along its long axis is shown in FIG. 4B. As shown, the stimulator (730) comprises two heads (731) and a body (732) that joins them. Each head (731) contains a stimulating electrode. The body of the stimulator (732) contains the electronic components and battery (not shown) that are used to generate the signals that drive the electrodes, which are located behind the insulating board (733) that is shown in FIG. 4B. However, in other embodiments of the invention, the electronic components that generate the signals that are applied to the electrodes may be separate, but connected to the electrode head (731) using wires. Furthermore, other embodiments of the invention may contain a single such head or more than two heads.

Heads of the stimulator (731) are applied to a surface of the patient's body, during which time the stimulator may be held in place by straps or frames (not shown), or the stimulator may be held against the patient's body by hand. In either case, the level of stimulation power may be adjusted with a wheel (734) that also serves as an on/off switch. A light (735) is illuminated when power is being supplied to the stimulator. An optional cap may be provided to cover each of the stimulator heads (731), to protect the device when not in use, to avoid accidental stimulation, and to prevent material within the head from leaking or drying.

Thus, in this embodiment of the invention, mechanical and electronic components of the stimulator (impulse generator, control unit, and power source) are compact, portable, and simple to operate.

Figure 4C:
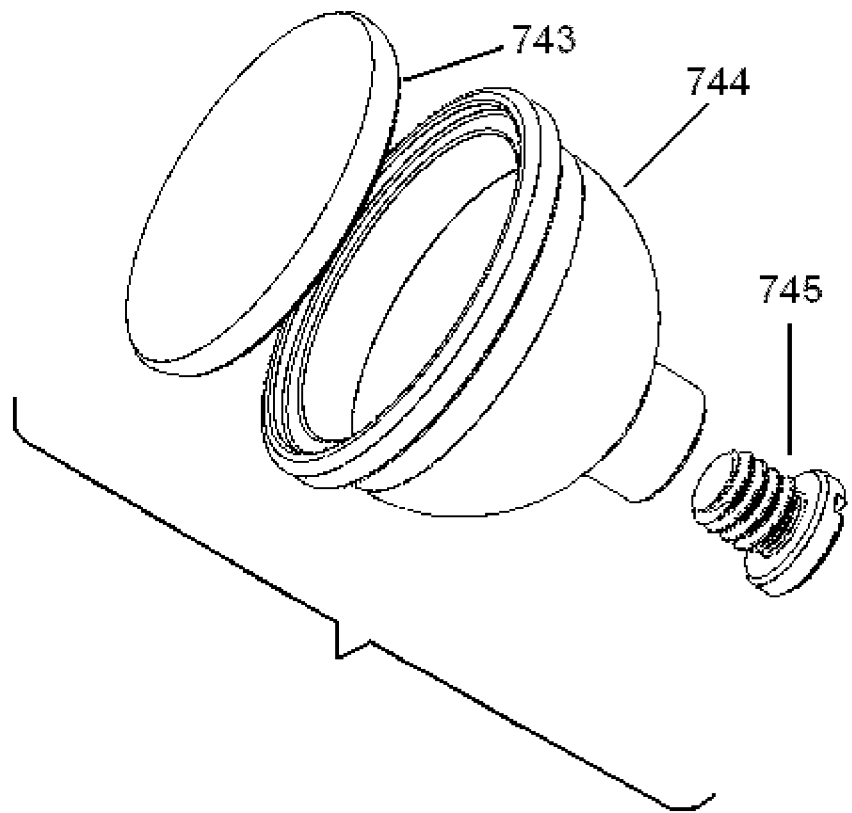
FIG. 4 illustrates a dual-electrode stimulator according to an embodiment of the present invention, which is shown to house the stimulator's electrodes and electronic components (A,B), as well as showing details of the head of the dual-electrode stimulator (C,D).
Figure 4D:
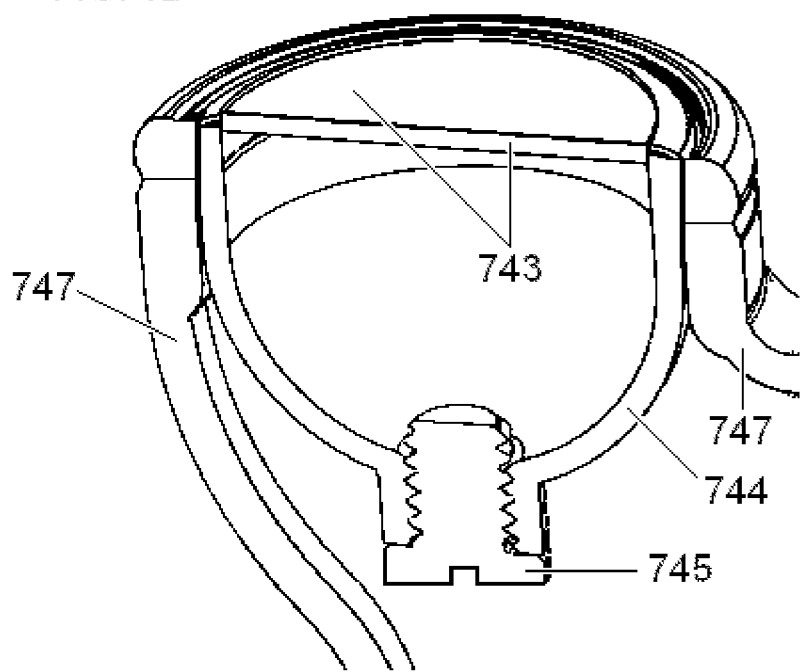

Details of one embodiment of the stimulator head are shown in FIGS. 4C and 4D. The electrode head may be assembled from a disc without fenestration (743), or alternatively from a snap-on cap that serves as a tambour for a dielectric or conducting membrane, or alternatively the head may have a solid fenestrated head-cup. The electrode may also be a screw (745). The preferred embodiment of the disc (743) is a solid, ordinarily uniformly conducting disc (e.g., metal such as stainless steel), which is possibly flexible in some embodiments. An alternate embodiment of the disc is a non-conducting (e.g., plastic) aperture screen that permits electrical current to pass through its apertures, e.g., through an array of apertures (fenestration). The electrode (745, also 340 in FIG. 2B) seen in each stimulator head may have the shape of a screw that is flattened on its tip. Pointing of the tip would make the electrode more of a point source, such that the equations for the electrical potential may have a solution corresponding more closely to a far-field approximation. Rounding of the electrode surface or making the surface with another shape will likewise affect the boundary conditions that determine the electric field. Completed assembly of the stimulator head is shown in FIG. 4D, which also shows how the head is attached to the body of the stimulator (747).

If a membrane is used, it ordinarily serves as the interface shown as 351 in FIG. 2B. For example, the membrane may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment, apertures of the disc may be open, or they may be plugged with conducting material, for example, KM10T hydrogel from Katecho Inc., 4020 Gannett Ave., Des Moines Iowa 50321. If the apertures are so-plugged, and the membrane is made of conducting material, the membrane becomes optional, and the plug serves as the interface 351 shown in FIG. 2B.

The head-cup (744) is filled with conducting material (350 in FIG. 2B), for example, SIGNAGEL Electrode Gel from Parker Laboratories, Inc., 286 Eldridge Rd., Fairfield N.J. 07004. The head-cup (744) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions that determine the electric field strength.

If an outer membrane is used and is made of conducting materials, and the disc (743) in FIG. 4C is made of solid conducting materials such as stainless steel, then the membrane becomes optional, in which case the disc may serve as the interface 351 shown in FIG. 2B. Thus, an embodiment without the membrane is shown in FIGS. 4C and 4D. This version of the device comprises a solid (but possibly flexible in some embodiments) conducting disc that cannot absorb fluid, the non-conducting stimulator head (744) into or onto which the disc is placed, and the electrode (745), which is also a screw. It is understood that the disc (743) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4D, these items are assembled to become a sealed stimulator head that is attached to the body of the stimulator (747). The disc (743) may screw into the stimulator head (744), it may be attached to the head with adhesive, or it may be attached by other methods that are known in the art. The chamber of the stimulator head-cup is filled with a conducting gel, fluid, or paste, and because the disc (743) and electrode (745) are tightly sealed against the stimulator head-cup (744), the conducting material within the stimulator head cannot leak out. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface (351 in FIG. 2B) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

In certain exemplary embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the surface of the dielectric material (e.g., with isopropyl alcohol or similar disinfectant), avoiding potential contamination during subsequent uses of the device. One such material is a thin sheet of Mylar, supported by a stainless steel disc, as described above.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a noninvasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIG. 2). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113 (1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-5182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25 (1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRI-SEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIG. 2). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25 (1987): 359-360; Yongmin KIM, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 2B) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
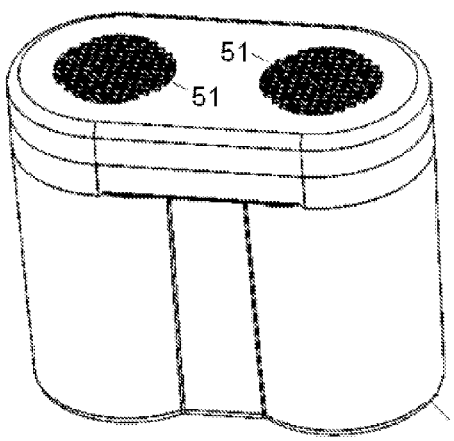
FIG. 5 illustrates an alternate embodiment of the dual-electrode stimulator (A-C), also comparing it with an embodiment of the magnetic stimulator according to the present invention (D).
Figure 5B:
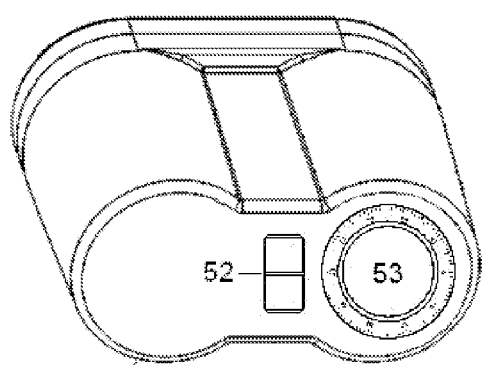
Figure 5C:
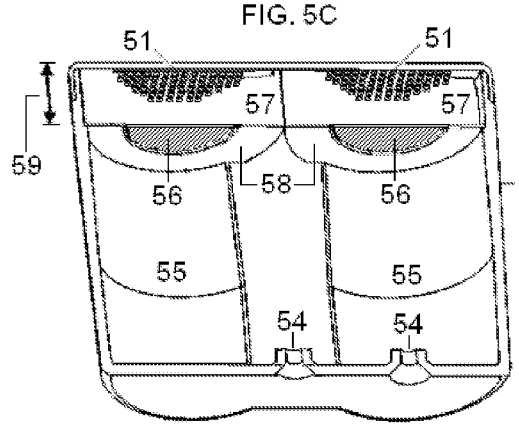

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 2B), and the power-level controller is attached to the control unit (330 in FIG. 2B) of the device. The power source battery and power-level controller, as well as the impulse generator (310 in FIG. 2B) are located (but not shown) in the rear compartment 55 of the housing of the stimulator 50.

Individual wires (not shown) connect the impulse generator (310 in FIG. 2B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 2B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In preferred embodiments of the electrode-based stimulator shown in FIG. 2B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008): 35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, the stimulator's conducting materials may be nonmagnetic, and the stimulator may be connected to the impulse generator by long nonmagnetic wires (345 in FIG. 2B), so that the stimulator may be used in the vicinity of a strong magnetic field, possibly with added magnetic shielding. As another example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

Although the electrode may consist of arrays of conducting material, the embodiments shown in FIGS. 4 and 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 4 and 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stokilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21 (1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71 (1999): 4944-4950]. In fact, patients found the design shown in FIGS. 4 and 5 to be less painful in a direct comparison with a commercially available grid-pattern electrode [UltraStim grid-pattern electrode, Axelggard Manufacturing Company, 520 Industrial Way, Fallbrook C A, 2011]. The embodiment of the electrode that uses capacitive coupling is particularly suited to the generation of uniform stimulation currents [Yongmin KIM, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 4 and 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 4 and 5 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 4 and 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in commonly assigned application US20110230938 (application Ser. No. 13/075, 746) entitled Devices and methods for non-invasive electrical stimulation and their use for vagal nerve stimulation on the neck of a patient, to SIMON et al., which is hereby incorporated by reference.

In one embodiment, the magnetic stimulator coil 341 in FIG. 2A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
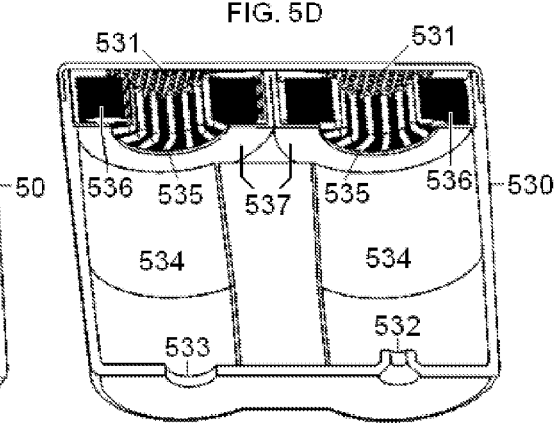

As seen in FIG. 5D, a mesh 531 has openings that permit a conducting gel (within 351 in FIG. 2A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 2A). The second opening is a conducting gel port 533 through which conducting gel (351 in FIG. 2A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 2A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Application of the Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

FIG. 6 illustrates use of the devices shown in FIGS. 3, 4 and 5 to stimulate the vagus nerve at that location in the neck, in which the stimulator device 50 or 530 in FIG. 5 is shown to be applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin.

The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Methods of treating a patient comprise stimulating the vagus nerve as indicated in FIGS. 6 and 7, using the electrical stimulation devices that are disclosed herein. Stimulation may be performed on the left or right vagus nerve or on both of them simulataneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6). The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. The pattern of a burst followed by silent inter-burst period repeats itself with a period of T. For example, the sinusoidal period may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 1 to 1000 microseconds (i.e., about 1 to 10 KHz), preferably 200 microseconds (about 5 KHz). A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. For most patients, the stimulation may be performed for 30 minutes and the treatment is performed once a week for 12 weeks or longer, because the progression of the disease from prodrome to true dementia is a chronic situation. The stimulation may also be performed as the need arises, before the patient undertakes a cognitive challenge. It is understood that parameters of the stimulation protocol may be varied in response to heterogeneity in the pathophysiology and needs of patients.

In other embodiments of the invention, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect.

For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Flickering light induces frequency-locked EEG activity that can resemble endogenous alpha waves and may even induce alpha-like activity, enhancing memory

[WILLIAMS J, Ramaswamy D, Oulhaj A. 10 Hz flicker improves recognition memory in older people. BMC Neurosci 7 (2006):21, pp. 1-7]. Such paired stimulation does not necessarily rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470(7332, 2011):101-104; PORTER B A, Khodaparast N, Fayyaz T, Cheung R J, Ahmed S S, Vrana W A, Rennaker R L 2nd, Kilgard M P. Repeatedly pairing vagus nerve stimulation with a movement reorganizes primary motor cortex. Cereb Cortex 22(10, 2012):2365-2374].

As noted above, the earliest stages of Alzheimer's disease are associated with olfactory regions of the brain, and as the disease progresses into mild cognitive impairment, the patient's sense of smell may deteriorate [WILSON R S, Arnold S E, Schneider J A, Boyle P A, Buchman A S, Bennett D A. Olfactory impairment in presymptomatic Alzheimer's disease. Ann NY Acad Sci 1170 (2009):730-735]. Testing of a patient's sense of smell may be performed by presenting a standard odorant to the nose of the patient, with each odorant diluted in a typically eight log-step concentration series. The stimulus concentrations are presented in an ascending series and sniffed from strips of blotter paper dipped into the odorant solutions. At a minimum, odor detection and recognition thresholds are measured for the patient [DOTY R L, Smith R, McKeown D A, Raj J. Tests of human olfactory function: principal components analysis suggests that most measure a common source of variance. Percept Psychophys 56(6, 1994): 701-707]. If the tests are performed annually beginning in early adulthood, the patient may at some point exhibit a deteriorating sense of smell, as evidenced by increased odor detection thresholds. At that point, or earlier if the patient has a family history of Alzheimer's disease, the present invention may be used in an effort to enhance or at least maintain the olfactory regions of the patient's brain, thereby serving as a prophylactic or treatment for AD. The disclosed method involves vagus nerve stimulation paired with the presentation of an odorant, at or above the measured odor detection threshold. The paired stimulation may be performed for 30 minutes and the treatment is performed once every two weeks for 12 weeks or longer. If after successive treatments the patient's sense of smell improves for an odorant, the process may be repeated with other odorants. One rationale for this method is that the mammalian main olfactory bulb receives a significant noradrenergic input from the locus ceruleus [LINSTER C, Nai Q, Ennis M. Nonlinear effects of noradrenergic modulation of olfactory bulb function in adult rodents. J. Neurophysiol. 2011 April; 105(4, 2011):1432-1443].

Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-455; CONWAY C R, Sheline Y I, Chibnall J T, George M S, Fletcher J W, Mintun M A. Cerebral blood flow changes during vagus nerve stimulation for depression. Psychiatry Res. 146(2, 2006):179-84]. Thus, by performing the imaging with different sets of stimulation parameters, a database may be constructed, such that the inverse problem of selecting parameters to match a particular brain region may be solved by consulting the database.

Stimulation waveforms may also be constructed by superimposing or mixing the burst waveform shown in FIG. 2, in which each component of the mixture may have a different period T, effectively mixing different burst-per-second waveforms. The relative amplitude of each component of the mixture may be chosen to have a weight according to correlations in different bands in an EEG for a particular resting state network. Thus, MANTINI et al performed simultaneous fMRI and EEG measurements and found that each resting state network has a particular EEG signature [see FIG. 3 in: MANTINI D, Perrucci M G, Del Gratta C, Romani G L, Corbetta M. Electrophysiological signatures of resting state networks in the human brain. Proc Natl Acad Sci USA 104(32, 2007):13170-13175]. They reported relative correlations in each of the following bands, for each resting state network that was measured: delta (1-4 Hz), theta (4-8 Hz), alpha (8-13 Hz), beta (13-30 Hz), and gamma (30-50 Hz) rhythms.

According to the present embodiment of the invention, multiple signals shown in FIG. 2 are constructed, with periods T that correspond to a location near the midpoint of each of the EEG bands (T equals approximately 0.4 sec, 0.1667 sec, 0.095 sec, 0.0465 sec, and 0.025 sec, respectively). A more comprehensive mixture could also be made by mixing more than one signal for each band. These signals are then mixed, with relative amplitudes corresponding to the weights measured for any particular resting state network, and the mixture is used to stimulate the vagus nerve of the patient. Phases between the mixed signals are adjusted to optimize the fMRI signal for the resting state network that is being stimulated. Stimulation of a network may activate or deactivate a network, depending on the detailed configuration of adrenergic receptors within the network and their roles in enhancing or depressing neural activity within the network, as well as subsequent network-to-network interactions. It is understood that variations of this method may be used when different combined fMRI-EEG procedures are employed and where the same resting state may have different EEG signatures, depending on the circumstances [WU C W, Gu H, Lu H, Stein E A, Chen J H, Yang Y. Frequency specificity of functional connectivity in brain networks. Neuroimage 42(3, 2008):1047-1055; LAUFS H. Endogenous brain oscillations and related networks detected by surface EEG-combined fMRI. Hum Brain Mapp 29(7, 2008):762-769; MUSSO F, Brinkmeyer J, Mobascher A, Warbrick T, Winterer G. Spontaneous brain activity and EEG microstates. A novel EEG/fMRI analysis approach to explore resting-state networks. Neuroimage 52(4, 2010): 1149-1161; ESPOSITO F, Aragri A, Piccoli T, Tedeschi G, Goebel R, Di Salle F. Distributed analysis of simultaneous EEG-fMRI time-series: modeling and interpretation issues. Magn Reson Imaging 27(8, 2009):1120-1130; FREYER F, Becker R, Anami K, Curio G, Villringer A, Ritter P. Ultra-high-frequency EEG during fMRI: pushing the limits of imaging-artifact correction. Neuroimage 48(1, 2009):94-108].

The individualized selection of parameters for the nerve stimulation protocol may based on trial and error in order to obtain a beneficial response without the sensation of pain or muscle twitches. Ordinarily, the amplitude of the stimulation signal is set to the maximum that is comfortable for the patient, and then the other stimulation parameters are adjusted. Alternatively, the selection of parameter values may involve tuning as understood in control theory, and as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Use of Control Theory Methods to Improve Treatment of Individual Patients

The vagus nerve stimulation may employ methods of control theory (e.g., feedback) in an attempt to compensate for motion of the stimulator relative to the vagus nerve; to avoid potentially dangerous situations such as excessive heart rate; and to maintain measured EEG bands (e.g., delta, theta, alpha, beta) within predetermined ranges, in attempt to preferentially activate particular resting state networks. Thus, with these methods, the parameters of the vagus nerve stimulation may be changed automatically, depending on physiological measurements that are made, in attempt to maintain the values of the physiological signals within predetermined ranges.

The effects of vagus nerve stimulation on surface EEG waveforms may be difficult to detect [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalograph measures. AIP Conf. Proc. DATA MINING, SYSTEMS ANALYSIS AND OPTIMIZATION IN BIOMEDICINE; Nov. 5, 2007, Volume 953, pp. 206-219], but they may exist nevertheless [KOO B. EEG changes with vagus nerve stimulation. J Clin Neurophysiol. 18(5, 2001): 434-41; KUBA R, Guzaninová M, Brázdil M, Novák Z, Chrastina J, Rektor I. Effect of vagal nerve stimulation on interictal epileptiform discharges: a scalp EEG study. Epilepsia. 43(10, 2002):1181-8; RIZZO P, Beelke M, De Carli F, Canovaro P, Nobili L, Robert A, Formaro P, Tanganelli P, Regesta G, Ferrillo F. Modifications of sleep EEG induced by chronic vagus nerve stimulation in patients affected by refractory epilepsy. Clin Neurophysiol. 115(3, 2004):658-64].

When stimulating the vagus nerve, motion variability is most often attributable to the patient's breathing, which involves contraction and associated change in geometry of the sternocleidomastoid muscle that is situated close to the vagus nerve (identified as 65 in FIG. 7). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 8 is a control theory representation of the disclosed vagus nerve stimulation methods. As shown there, the patient, or the relevant physiological component of the patient, is considered to be the "System" that is to be controlled. The "System" (patient) receives input from the "Environment." For example, the environment would include ambient temperature, light, and sound. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may include the control unit 330 in FIG. 2. Feedback in the schema shown in FIG. 8 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34 (2010):195-212]. In the present application, the features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov PCh, Mark R G, Mietus J E, Moody G B, Peng C K, Stanley H E. PhysioBank, PhysioToolkit, and PhysioNet: Components of a New Research Resource for Complex Physiologic Signals. Circulation 101 (23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration.

It may be therapeutically advantageous to program the control unit 330 to control the impulse generator 310 in such a way as to temporally modulate stimulation by the magnetic stimulator coils or electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the problem of dementia that is addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

Patent application publication US2009/0177252, entitled Synchronization of vagus nerve stimulation with the cardiac cycle of a patient, to Arthur D. Craig, discloses a method of treating a medical condition in which the vagus nerve is stimulated during a portion of the cardiac cycle and the respiratory cycle. That disclosure pertains to the treatment of a generic medical condition, so it is not specifically directed to the treatment of dementia.

In some embodiments of the invention, overheating of the magnetic stimulator coil may also be minimized by optionally restricting the magnetic stimulation to particular phases of the respiratory cycle, allowing the coil to cool during the other phases of the respiratory cycle. Alternatively, greater peak power may be achieved per respiratory cycle by concentrating all the energy of the magnetic pulses into selected phases of the respiratory cycle.

Furthermore, as an option in the present invention, parameters of the stimulation may be modulated by the control unit 330 to control the impulse generator 310 in such a way as to temporally modulate stimulation by the magnetic stimulator coil or electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the magnetic stimulator coil or electrodes, in such a way as to achieve and maintain the blood pressure within predetermined safe or desired limits, by the same method that was indicated above for the heart rate. Thus, even if one does not intend to treat dementia, embodiments of the invention described above may be used to achieve and maintain the heart rate and blood pressure within desired ranges.

Let the measured output variables of the system in FIG. 8 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i = r_i - y_i$ is small, even if there is environmental input or noise to the system. Consider the error function $e_i = r_i - y_i$ to be the sensed physiological input to the controller in FIG. 8 (i.e., the reference signals are integral to the controller, which subtracts the measured system values from them to construct the control error signal). The controller will also receive a set of measured environmental signals $v_k$ (k=1 to R), which also act upon the system as shown in FIG. 8.

The functional form of the system's input u(t) is constrained to be as shown in FIGS. 2D and 2E. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. One or more accelerometer is attached to the patient's neck, and one or more accelerometer is attached to the head of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118(1, 1998):82-5]. The ultrasound probe is configured to have the same shape as the stimulator, including the attachment of one or more accelerometer. As part of the preliminary protocol, the patient with accelerometers attached is then instructed to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmur ̧o, Przemys ̧aw P ̧onecki, Jacek Starzyński, Stanis ̧law Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form $dy_i/dt = F_i(t, \{y_i\}, \{u_j\}, \{v_k\}; \{r_i\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form: $u(t) = K_p e(t) + K_i \int_0^t e(\tau) d\tau + K_d de/dt$ where the parameters for the controller are the proportional gain ($K_r$), the integral gain ($K_i$) and the derivative gain ($K_d$). This type of controller, which forms a controlling input signal with feedback using the error e=r−y, is known as a PID controller (proportional-integral-derivative).

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G.C.Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu X U E, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

Commercial versions of PID controllers are available, and they are used in 90% of all control applications. To use such a controller, for example, in an attempt to maintain the EEG gamma band at a particular level relative to the alpha band, one could set the integral and derivative gains to zero, increase the proportional gain (amplitude of the stimulation) until the relative gamma band level starts to oscillate, and then measure the period of oscillation. The PID would then be set to its tuned parameter values.

Although classical control theory works well for linear systems having one or only a few system variables, special methods have been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the controller shown in FIG. 8 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

The controller shown in FIG. 8 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 8 may be a type of predictive controller, methods for which have been developed in other contexts as well, such as when a model of the system is used to calculate future outputs of the system, with the objective of choosing among possible inputs so as to optimize a criterion that is based on future values of the system's output variables.

Performance of system control can be improved by combining the feedback closed-loop control of a PID controller with feed-forward control, wherein knowledge about the system's future behavior can be fed forward and combined with the PID output to improve the overall system performance. For example, if the sensed environmental input in FIG. 8 is such the environmental input to the system will have a deleterious effect on the system after a delay, the controller may use this information to provide anticipatory control input to the system, so as to avert or mitigate the deleterious effects that would have been sensed only after-the-fact with a feedback-only controller.

A mathematical model of the system is needed in order to perform the predictions of system behavior, e.g., make predictions concerning the onset of a cognitive fluctuation in a dementia patient. Models that are completely based upon physical first principles (white-box) are rare, especially in the case of physiological systems. Instead, most models that make use of prior structural and mechanistic understanding of the system are so-called grey-box models. If the mechanisms of the systems are not sufficiently understood in order to construct a white or grey box model, a black-box model may be used instead. Such black box models comprise autoregressive models [Tim BOLLERSLEV. Generalized autoregressive conditional heteroskedasticity. Journal of Econometrics 31 (1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48 (1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14 (1998): 35-62].

For the present invention, if a black-box model must be used, the preferred model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs [Christopher J. C. BURGES. A tutorial on support vector machines for pattern recognition. Data Mining and Knowledge Discovery 2 (1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4(2, 2009): 24-38; PRESS, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

In this example, a training set of physiological data will have been acquired that includes whether or not the patient is experiencing a cognitive fluctuation. Thus, the classification of the patient's state is whether or not the fluctuation is in progress, and the data used to make the classification consist of the acquired physiological data: EEG and its derived features; respiration (abdominal and thoracic plethysmography), carbon dioxide (capnometry with nasual cannula), heart rate (electrocardiogram leads), skin impedance (electrodermal leads), vocalization (microphones), light (light sensor), motion (accelerometer), external and finger temperature (thermometers), etc., as well as parameters of the stimulator device (if it is currently being used on a patient experiencing a fluctuation), evaluated at $\Delta$ time units prior to the time at which binary "in fluctuation" (yes/no) data are acquired, as indicated by the patient or a caregiver. Thus, for a patient who is experiencing a fluctuation, the SVM is trained to forecast the termination of fluctuation, $\Delta$ time units into the future, and the training set includes the time-course of features extracted from the above-mentioned physiological signals. For a patient who is not experiencing a cognitive fluctuation, the SVM is trained to forecast the imminence of a fluctuation, $\Delta$ time units into the future, and the training set includes the above-mentioned physiological signals. After training the SVM, it is implemented as part of the controller. For patients who are not experiencing a fluctuation, the controller may sound an alarm and advise the use of vagal nerve stimulation, whenever there is a forecast of an imminent cognitive fluctuation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating or preventing dementia in a patient, the method comprising:
positioning one or more electrodes in contact with an outer skin surface of a neck of the patient, wherein a housing includes an exterior portion and an interior portion, wherein the exterior portion includes the one or more electrodes, wherein the interior portion contains a power source coupled to the one or more electrodes;
generating an electric current with the power source; and
transmitting, during the positioning, the electric current non-invasively and transcutaneously from the power source via the one or more electrodes through the outer skin surface of the neck to a vagus nerve in the patient, wherein the electric current comprises a single signal comprising bursts of pulses with each of the pulses having a duration from about 20 microseconds to about 1000 microseconds and each of the bursts followed by a silent intra-burst period such that each of the bursts has a frequency from about 15 Hz to about 50 Hz, and wherein the electric current is sufficient to modify dementia within the patient.

2. The method of claim 1, wherein the housing comprises a conducting medium, wherein the transmitting is through the conducting medium.

3. The method of claim 1, further comprising:
generating an electric field at or near the housing; and
shaping the electric field such that the electric field is sufficient to modulate a nerve fiber at a target region; and wherein the electric field is not sufficient to substantially modulate a nerve or muscle between the skin surface and the target region.

4. The method of claim 3 wherein the electric field at the vagus nerve is about 10 to about 600 V/m.

5. The method of claim 4 wherein the electric field is less than 100 V/m.

6. The method of claim 3 wherein the vagus nerve is at least approximately 0.5-2 cm below an outer skin-surface of the patient.

7. The method of claim 1 wherein each of the bursts contains from about 1 pulse to about 20 pulses.

8. The method of claim 1 wherein the pulses are full sinusoidal waves.

9. The method of claim 1 wherein the duration of a pulse within a burst is about 200 microseconds, wherein a number of pulses per burst is from about 4 to about 6, and wherein a number of bursts per second is from about 20 to about 30.

10. The method of claim 1 wherein afferent nerve fibers of the vagus nerve are stimulated.

11. The method of claim 1 wherein the electric current generates an electric field at the vagus nerve above a threshold for generating action potentials within A and B fibers of the vagus nerve and below a threshold for generating action potentials within C fibers of the vagus nerve.

12. The method of claim 1 wherein the electric current generates an electric field at the vagus nerve above a threshold for generating action potentials within fibers of the vagus nerve responsible for activating neural pathways causing release of inhibitory neurotransmitters within a brain of the patient.

13. The method of claim 12 wherein the inhibitory neurotransmitters comprise norepinephrine.

14. The method of claim 13 wherein the norepinephrine is released into a resting state neural network of the patient.

15. The method of claim 14 wherein the resting state network is a default mode network or a ventral attention network.

16. The method of claim 13 wherein the norepinephrine counteracts neuroinflammation in or around a locus ceruleus of the patient.

* * * * *